US009932368B2

United States Patent
Albericio Palomera et al.

(10) Patent No.: US 9,932,368 B2
(45) Date of Patent: Apr. 3, 2018

(54) PEPTIDES FOR THE STIMULATION OF COLLAGEN FORMATION

(71) Applicants: INFINITEC ACTIVOS S.L, Montornés del Vallés—Barcelona (ES); PEPTIDEPHARMA NOVA SL, Barcelona (ES)

(72) Inventors: Fernando Albericio Palomera, Barcelona (ES); Gerardo Alexis Acosta Crespo, Barcelona (ES)

(73) Assignee: INFINITEC ACTIVOS S.L., Barcelona (ES)

( * ) Notice: Subject to any disclaimer, the term of this patent is extended or adjusted under 35 U.S.C. 154(b) by 64 days.

(21) Appl. No.: 14/909,591

(22) PCT Filed: Jul. 31, 2014

(86) PCT No.: PCT/EP2014/066448
§ 371 (c)(1),
(2) Date: Feb. 2, 2016

(87) PCT Pub. No.: WO2015/014923
PCT Pub. Date: Feb. 5, 2015

(65) Prior Publication Data
US 2016/0185819 A1 Jun. 30, 2016

(30) Foreign Application Priority Data
Aug. 2, 2013 (EP) ..................... 13382316

(51) Int. Cl.
*A61K 8/64* (2006.01)
*A61Q 7/00* (2006.01)
*A61Q 19/08* (2006.01)
*C07K 7/06* (2006.01)

(52) U.S. Cl.
CPC ................. *C07K 7/06* (2013.01); *A61K 8/64* (2013.01); *A61Q 7/00* (2013.01); *A61Q 19/08* (2013.01)

(58) Field of Classification Search
None
See application file for complete search history.

(56) References Cited

FOREIGN PATENT DOCUMENTS

WO    2012168519 A1    12/2012

OTHER PUBLICATIONS

International Search Report, dated Oct. 31, 2014.
Johnson, Wilbur, et al.; "Safety Assessment of Palmitoyl Oligopeptides as Used in Cosmetics," Cosmetic Ingredient Review, 2012, pp. 1-22.
Löwik, Dennis W.P.M., et al.; "Tuning Secondary Structure and Self-Assembly of Amphiphilic Peptides," Langmuir, 2005, pp. 524-526, vol. 21.
Hamley, I; "Self-assembly of amphiphilic peptides," Soft Matter, 2011, pp. 4122-4138, vol. 7.
Berge, Stephen M., et al.; "Pharmaceutical Salts," Journal of Pharmaceutical Sciences, 1977, pp. 1-19, vol. 66.
Dixon, H.B.F, et al.; "Nomenclature and Symbolism for Amino Acids and Peptides," IUPAC-IUB Joint Commission on Biochemical Nomenclature (JCBN), Eur. J. Biochem., 1984, pp. 9-37, vol. 138.
Embil, K., et al.; "The Microsponge® Delivery System (MDS): a topical delivery system with reduced irritancy incorporating multiple triggering mechanisms for the release of actives," J. Microencapsulation, 1996, pp. 575-588, vol. 13.

*Primary Examiner* — Kevin S Orwig
(74) *Attorney, Agent, or Firm* — Tristan A. Fuierer; Moore & Van Allen, PLLC

(57) ABSTRACT

The present invention relates to a compound of formula (I) ($R_1$-Arg-Gly-Asp-Gly-Ala-Asn-Pro-Asn-Ala-Ala-Gly-$R_2$), formula II ($R_5$-Arg-Gly-Asp-Gly-Pro-Gln-Gly-Pro-Gln-$R_6$), or formula III ($R_9$-Trp-Arg-Phe-Gln-Trp-Gln-Phe-Glu-Gln-$R_{10}$), and to compositions comprising a compound of formulas I, II or III, as well as the use of said compounds and/or said compositions in the cosmetic treatment of skin and/or hair, and to the use thereof for inducing the formation of collagen.

18 Claims, 4 Drawing Sheets

Figure 3A
Figure 3B
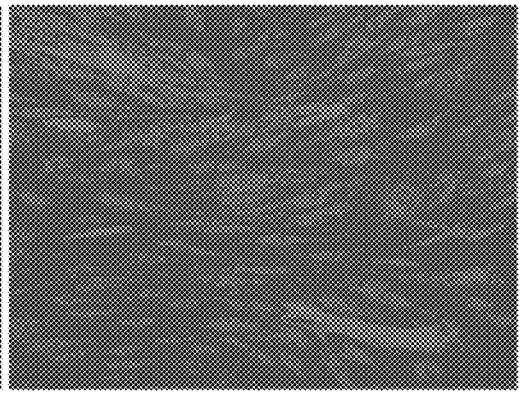
Figure 3C
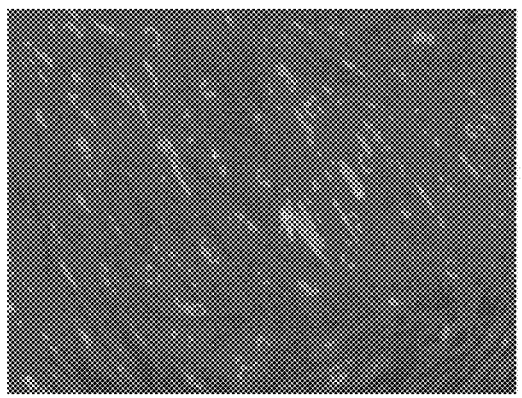
Figure 3D
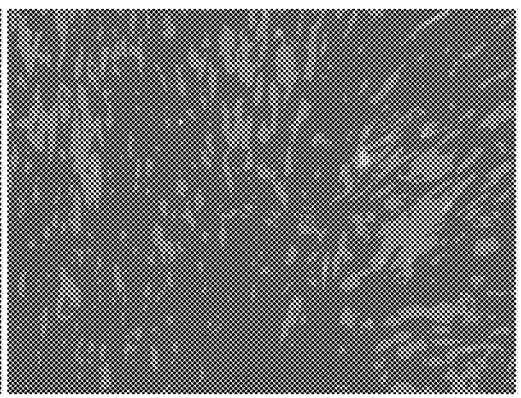
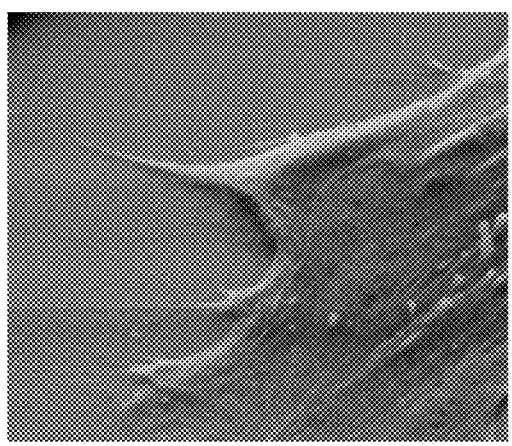
FIG. 4A
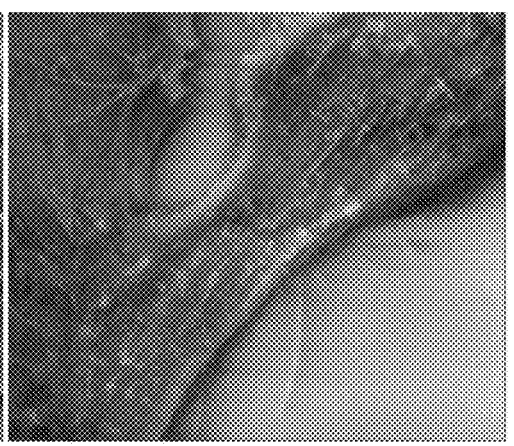
FIG. 4B

PEPTIDES FOR THE STIMULATION OF COLLAGEN FORMATION

CROSS-REFERENCE TO RELATED APPLICATIONS

This application is filed under the provisions of 35 U.S.C. § 371 and claims the priority of International Patent Application No. PCT/EP2014/066448 filed on 31 Jul. 2014 entitled "PEPTIDES FOR THE STIMULATION OF COLLAGEN FORMATION" in the name of Fernando ALBERICIO PALOMERA, et al., which claims priority to European Patent Application No. 13382316.1, filed on 02 Aug. 2013, both of which are hereby incorporated by reference herein in their entirety.

FIELD OF THE INVENTION

The present invention relates to a compound and to compositions comprising said compound that are capable of stimulating collagen formation, as well as the use of said compound and/or said compositions in the cosmetic treatment of skin and/or hair, in particular, in the prevention of ageing and stimulation of hair growth.

BACKGROUND OF THE INVENTION

The aim of cosmetic products is providing skin and hair care, improving the properties, appearance an functions thereof, as well as providing beauty and wellness to our body, especially to the face and neck.

Ageing and other external factors may affect the functions and appearance of skin. Thus, there is a great variety of cosmetics and pharmaceutical products that are used in order to avoid such effects.

The world of cosmetics, including the development of a wide range of skin care products, which consequently helps to improve human life, is starting a new era with technological and scientific support for the skin in its integrity as an organ, and the scalp and a correct interaction with everything, day to day life, stress, and normal ageing, and hair loss.

The aim of the present invention refers to novel active peptides that are capable of improving the properties, aspect and functions of the skin and/or hair due to their capability of inducing the production of collagen types I, III, IV, VIII by the fibroblasts. Also, the new active peptides can stimulate the proliferation of new hair by stimulation of hair follicle to induce proliferation, dermal papilla and/or stem cells regulation, which are the key to the generation of new hair Several products comprising peptides to stimulate collagen biosynthesis have been described in the state of the art review of W. Johnson, Jr. ["Safety Assessment of Palmitoyl Oligopeptides as Used in Cosmetics", Cosmetic Ingredient Review, 13 Aug. 2012, Washington], wherein several palmitoyl peptides are described, said peptides being different from the compounds of the present invention. Additionally, International patent application WO 2012/168519 A1 describes the use of peptides to stimulate collagen biosynthesis but the document fails to provide any detailed information of said peptides which enables the skilled in the art to reproduce the invention.

There is a need in the art to provide novel compounds that stimulate collagen synthesis and their use in the treatment of skin and hair. The present invention solves this need by a peptide of formula (I), as defined below.

SUMMARY OF THE INVENTION

In the first aspect, the present invention refers to a compound of formula (I):

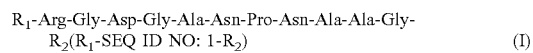

$R_1$-Arg-Gly-Asp-Gly-Ala-Asn-Pro-Asn-Ala-Ala-Gly-$R_2$($R_1$-SEQ ID NO: 1-$R_2$)  (I)

wherein $R_1$ is selected from the group consisting of H, $C_1$-$C_{24}$ alkyloyl, $C_2$-$C_{24}$ alkenyloyl, and $C_6$-$C_{10}$ aryl;

$R_2$ is selected from the group consisting of —$OR_3$, —$SR_3$, —$NR_3R_4$, and a polymer derived from polyethylene glycol;

$R_3$ and $R_4$ are independently selected from the group consisting of H; $C_1$-$C_6$ alkyl; $C_3$-$C_8$ cycloalkyl; $C_6$-$C_{10}$ aryl; $C_6$-$C_{10}$ aryl-$C_1$-$C_6$ alkyl; 5, 6 or 7 membered heterocycle containing 1, 2 or 3 heteroatoms in the ring independently selected from the group consisting of N, O and S; 5 or 6 membered monocyclic heteroaryl containing 1, 2, 3 or 4 heteroatoms in the ring independently selected from the group consisting of N, O and S; 8, 9 or 10 membered bicyclic heteroaryl containing 1, 2, 3 or 4 heteroatoms independently selected from the group consisting of N, O and S; heteroaryl-$C_1$-$C_3$ alkyl, wherein the heteroaryl is monocyclic or bicyclic as previously defined;

its stereoisomers, its cosmetically acceptable salts, or mixtures thereof.

In the second aspect, the invention refers to a composition which comprises a compound as defined in the first aspect and a cosmetically acceptable excipient.

In the third aspect, the invention refers to the use of a compound of formula (I) as defined in the first aspect, or a composition as defined in the second aspect, for the cosmetic non-therapeutic treatment and/or care of skin and/or hair. This aspect may be also formulated as a method of cosmetic non-therapeutic treatment and/or care of skin and/or hair which comprises applying to the skin and/or hair a compound of formula (I) as defined in the first aspect, or of a composition, as defined in the second aspect.

In the fourth aspect, the invention refers to the use of a compound of formula (I) as defined in the first aspect, or a composition as defined in the second aspect, for the induction of collagen formation.

DESCRIPTION OF THE DRAWINGS

FIG. 3 shows the fluorescence microscopy study of the induction of collagens in human dermal fibroblasts by the mixture of the three peptides 1-3. A) Collagen I expression in an untreated human dermal fibroblast control. B) Collagen I expression in human dermal fibroblasts treated with a mixture of peptides 1-3. C) Collagen VI expression in an untreated human dermal fibroblast control. D) Collagen VI expression in human dermal fibroblasts treated with the mixture of the three peptides 1-3.

FIG. 4 shows the scanning electron microscopy study of the induction of collagens in human dermal fibroblasts using the mixture of the three peptides 1-3 of Example 1. A: untreated human dermal fibroblasts. B: human dermal fibroblasts treated with a mixture of peptides 1-3 where the formation of collagen fibrils around the cell membrane is clearly observed.

DETAILED DESCRIPTION OF THE INVENTION

Figure 1:
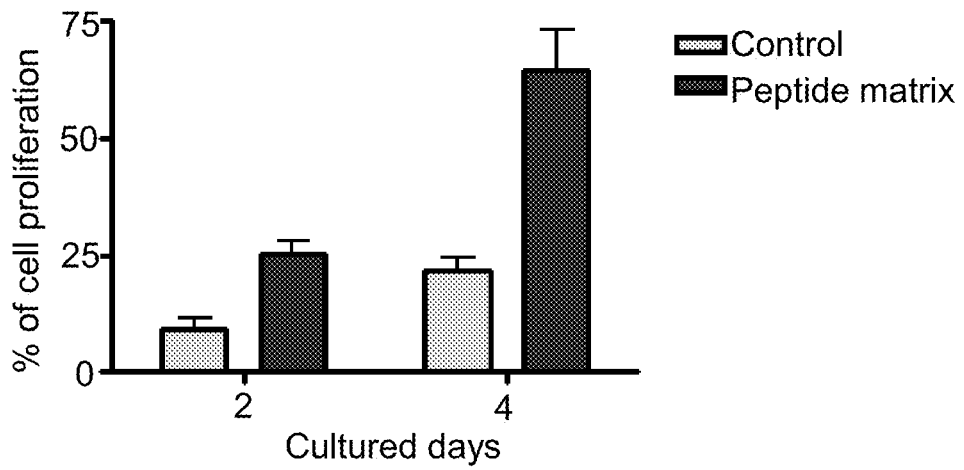
FIG. 1 shows a cell multiplication and amplification study using a mixture of the three peptides 1-3. The results were evaluated after 2 and 4 days of treatment with the peptides.

"Alkyl" refers to a straight or branched hydrocarbon chain radical consisting of carbon and hydrogen atoms, containing no unsaturation, having 1 to 16, preferably 1 to 6, more preferably 1 to 3 carbon atoms, and which is attached to the rest of the molecule by a single bond, e.g., methyl, ethyl, n-propyl, i-propyl, n-butyl, t-butyl, and n-pentyl.

"Alkyloyl" refers to a straight or branched hydrocarbon chain radical consisting of carbon and hydrogen atoms, containing no unsaturation, having 1 to 24, preferably 10 to 24 carbon atoms, and which is attached to the rest of the molecule by —C(O)— group, e.g., caproyl ($CH_3$—$(CH_2)_8$—C(O)—), lauroyl ($CH_3$—$(CH_2)_{10}$—C(O)—), myristoyl ($CH_3$—$(CH_2)_{12}$—C(O)—), palmitoyl (Palm) ($CH_3$—$(CH_2)_{14}$—C(O)—), stearoyl ($CH_3$—$(CH_2)_{16}$—C(O)—), arachidoyl ($CH_3$—$(CH_2)_{18}$—C(O)—) and behenoyl ($CH_3$—$(CH_2)_{20}$—C(O)—).

"Alkenyloyl" refers to a straight or branched hydrocarbon chain radical consisting of carbon and hydrogen atoms, containing one or more unsaturations, having 1 to 24, preferably 10 to 24 carbon atoms, and which is attached to the rest of the molecule by —C(O)— group, e.g., myristoleyl ($CH_3(CH_2)_3CH$=$CH(CH_2)_7C(O)$—), palmitoleyl ($CH_3(CH_2)_5CH$=$CH(CH_2)_7C(O)$—), oleyl ($CH_3(CH_2)_7CH$=$CH(CH_2)_7C(O)$—), and linoleyl ($CH_3(CH_2)_4CH$=$CHCH_2CH$=$CH(CH_2)_7C(O)$—).

"Aryl" refers to an aromatic hydrocarbon radical having 6 to 10 carbon atoms such as phenyl or naphthyl.

"Aryl-alkyl" refers to an alkyl radical, as defined above, attached to an aryl radical, as defined above, such as benzyl.

"Cycloalkyl" refers to a saturated carbocyclic ring having from 3 to 8 carbon atoms.

"Heteroaryl" refers to a 5 or 6 membered monocyclic aromatic ring or 8, 9 or 10 membered bicyclic aromatic ring, which contains carbon atoms and 1, 2, 3 or 4 heteroatoms in the ring independently selected from the group consisting of N, O and S, such as pyridine.

"Heteroarylalkyl" refers to an alkyl radical, as defined above, attached to a heteroaryl radical, as defined above.

"Heterocycle" refers to a 5, 6 or 7 membered, saturated or partially saturated ring, which contains carbons atoms and 1, 2 or 3 heteroatoms in the ring independently selected from the group consisting of N, O and S. Examples of heterocycles are benzimidazole, benzothiazole, furan, isothiazole, imidazole, indole, piperidine, piperazine and morpholine.

"Polymer derived from polyethylene glycol" refers to a (—$CH_2$—$CH_2$—O)$_n$—H radical, wherein n is a number between 4 and 250.

"Stereoisomer" refers to compound consisting of the same atoms attached with the same bond sequence but having different tridimensional structures that cannot be interchanged, such as R/S and cis/trans (Z/E) configuration.

The term "cosmetically acceptable salts" means a salt recognized for its use in human beings, and includes salts used to form base addition salts, either inorganic or organic, or acid addition salts, either inorganic or organic. It is to be noted that, since safety requirements for pharmaceuticals are more stringent than those for cosmetics, any pharmaceutically acceptable salt will also be a cosmetically acceptable salt. The nature of the salt is not critical, provided that it is cosmetically or pharmaceutically acceptable. The cosmetically or pharmaceutically acceptable salts of the peptides of the invention can be obtained by the conventional methods, well known in the prior art [Berge S. M. et al., "Pharmaceutical Salts", (1977), J. Pharm. Sci., 66, 119].

Additionally, it will be appreciated that non-cosmetically acceptable salts also fall within the scope of the invention since said non-cosmetically acceptable salts may be useful precursors in the preparation of cosmetically acceptable salts. The preparation of salts can be carried out by methods known in the art. For instance, cosmetically acceptable salts of compounds provided herein may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, ammonium, and organic alkali salts such as, for example, ethylenediamine, ethanolamine, N,N-dialkylenethanolamine, triethanolamine, glucamine and basic aminoacids salts. Examples of the metallic salts include, for example, sodium, potassium, calcium, magnesium, aluminium and lithium salts.

"Cosmetically acceptable excipients" refer to excipients that are physiologically tolerated and that do not produce any undesired allergic or similar reaction when topically applied to a human. Preferably, as used herein, it means that said excipient is included in the European Commission database for cosmetic substances an ingredients CosIng.

"Treatment" as used herein qualified as "cosmetic non-therapeutic" refers to the application of the compound to skin and/or hair in particular for improving the cosmetic quality of the skin and/or hair, such as, without limiting, the moisture rate, elasticity, firmness, brightness, tone or texture thereof, among others.

"Care" refers to the maintenance of the qualities of skin and/or hair. Said qualities may be improved or maintained by a cosmetic treatment and/or care of skin and/or hair.

"Prevention" refers to the ability of a compound of the invention in preventing, delaying ageing and/or hair loss.

"Ageing" refers to the changes experienced by the skin with age (chronoaging) or through exposure to the sun (photoaging) or to environmental agents such as tobacco smoke, to extreme environmental climatic conditions of cold or wind, chemical contaminants or pollutants, and includes all the external visible and/or perceptible changes through touch, such as and not restricted to, the development of discontinuities on the skin such as wrinkles, fine lines, expression lines, stretch marks, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, hair loss, orange peel skin, loss of collagen structure, among others. The term "photoaging" groups together the set of processes due to the prolonged exposure of the skin to ultraviolet radiation which result in the premature aging of the skin, and it presents the same physical characteristics as aging, such as and not restricted to, flaccidity, sagging, changes to the color or irregularities in the pigmentation, abnormal and/or excessive keratinization. The sum of several environmental factors such as exposure to tobacco smoke, exposure to pollution, and climatic conditions such as cold and/or wind also contributes to the aging of the skin.

In this description the abbreviations used for amino acids follow the recommendations of the 1983 IUPAC-IUB Commission of Biochemical Nomenclature specified in Eur. J. Biochem., (1984), 138, 937.

Thus, for example, Arg or R represents $NH_2$—$CH(CH_2$—$CH_2$—$CH_2$—NH—$C(=NH)NH_2)$—COOH, Arg- or R— represents $NH_2$—$CH(CH_2$—$CH_2$—$CH_2$—NH—$C(=NH)$ $NH_2)$—CO—, -Arg or —R represents —NH—$CH(CH_2$—$CH_2$—$CH_2$—NH—$C(=NH)NH_2)$—COOH, and -Arg- or —R— represents —NH—$CH(CH_2$—$CH_2$—$CH_2$—NH—C($=NH)NH_2$)—CO—. Therefore, the hyphen, which represents the peptide bond, eliminates the OH in the 1 carboxyl group of the amino acid (represented here in the conventional non-ionized form) when situated to the right of the symbol, and eliminates the H of the 2 amino group of the amino acid when situated to the left of the symbol; both modifications can be applied to the same symbol (see Table 1).

The aminoacids are named using the conventional nomenclature in one and three letter codes, as follows:
alanine, Ala o A,
cysteine, Cys o C,
aspartic acid, Asp o D,
glutamic acid, Glu o E,
phenylalanine, Phe o F,
glycine, Gly o G,
histidine, His o H,
isoleucine, Ile o I,
lysine, Lys o K,
leucine, Leu o L,
methionine, Met o M,
asparagine, Asn o N,
proline, Pro o P,
glutamine, Glu o Q,
arginine, Arg o R,
serine, Ser o S,
threonine, Thr o T,
valine, Val o V,
tryptophan, Trp o W, y
tyrosine, Tyr o Y.

In the first aspect, the invention refers to a compound of formula (I), as defined above.

Preferably $R_1$ is selected from the group consisting of H, $C_{10}$-$C_{24}$ alkyloyl and $C_{10}$-$C_{24}$ alkenyloyl; more preferably from the group consisting of caproyl ($CH_3$—$(CH_2)_8$—C(O)—), lauroyl ($CH_3$—$(CH_2)_{10}$—C(O)—), myristoyl ($CH_3$—$(CH_2)_{12}$—C(O)—), palmitoyl ($CH_3$—$(CH_2)_{14}$—C(O)—), stearoyl ($CH_3$—$(CH_2)_{16}$—C(O)—), arachidoyl ($CH_3$—$(CH_2)_{18}$—C(O)—) and behenoyl ($CH_3$—$(CH_2)_{20}$—C(O)—); still more preferably, $R_1$ is palmitoyl.

Preferably $R_2$ is selected from the group consisting of —$OR_3$, —$SR_3$, —$NR_3R_4$, wherein $R_3$ and $R_4$ are independently selected from the group consisting of H and $C_1$-$C_6$ alkyl; more preferably $R_2$ is selected from the group consisting of —OH, —SH, —$NH_2$; still more preferably $R_2$ is $NH_2$.

In a preferred embodiment, $R_1$ is palmitoyl and $R_2$ is —$NH_2$, i.e., the compound of formula (I) is a peptide having the sequence Palm-RGDGANPNAAG-$NH_2$, (Palm-SEQ ID NO: 1—$NH_2$).

In the second aspect, the invention refers to a composition comprising a compound as previously defined and a cosmetically acceptable excipient.

In a preferred embodiment the cosmetically acceptable excipient(s) is(are) selected from the group consisting of humectants, emollients, rheological modifiers, perfumes, essential oils, preserving agents, solvents, emulsifiers, silicones, antioxidants, chelating agents, vitamins and mixtures thereof.

The composition of the invention may comprise humectants for preserving the moisture of the composition. Humectants in the context of the present invention may be selected, among other, from polyols, such as glycerol, glycerol polymers, diols, polyethylene glycols, alcoholic sugars, sugars, other polyols, and mixtures thereof. Examples of moistening agents are glycerol (1,2,3-propanetriol), propylene glycol, glycols, polyethylene glycols and mixtures thereof.

"Glycerin" or "glycerol" refers to 1,2,3-propanetriol.

"Glycerin polymers" refers to compounds having from 3 to 40 glycerin units, such as polyglycerin-3, polyglycerin-4, polyglycerin-6, polyglycerin-10, polyglycerin-20 y polyglycerin-40.

"Diols" define $C_2$-$C_4$ alkyls substituted with two hydroxyl groups. Examples of diols are butylene glycols such as 1,2-butanediol, 1,3-butanediol, 1,4-butanediol and 2,3-butanediol.

"Polyethylene glycol" or "PEG" refers to an oligomer or polymer of ethylene oxide having from 4 to 240 units of ethylene glycol, such as PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240; methoxylated polyethylene glycols, such as methoxy PEG-7, methoxy PEG-10, methoxy PEG-16, methoxy PEG-25, methoxy PEG-40, methoxy PEG-100; and glycerin polyethylene glycols, i.e., glycerin that has been etherified with 7 to 40 units of ethylene glycol, such as glycereth-7, glycereth-8, glycereth-12, glycereth-18, glycereth-20, glycereth-26 and glycereth-31.

"Alcoholic sugars" refers to polyols having the general formula H(HCO)$_{n+1}$H, such as erythritol, isomalt, lactitol, maltitol, mannitol, sorbitol and xylitol.

"Sugars" refers to monosaccharides and polysaccharides, such as amylose, fructose, glucose, mannose, lactose, ribose, saccharose, trehalose and xylose.

The composition according to the invention may comprise emolients for smoothening the skin. In the context of the present invention, emolients may be selected, among others, from alkanes and esters, such as glycerides, propylene glycol esters, alkyl esters, ethers, glycols, and mixtures thereof. Examples of emolients are cocoglycerides, $C_{12}$-$C_{15}$ alkyl benzoate, glycols, polyethylene glycols, ethers, glycerides, caprilates, $C_{12}$-$C_{15}$ alkyls.

"Glycerides" refers to mono, di and triesters of glycerin with acids, such as monoglycerides, for examples, glyceryl adipate, glyceryl caprate, glyceryl caprilate, glyceryl cocoate, glyceryl ethylhexanate, glyceryl heptanate, glyceryl isostearate, glyceryl lanolate, glyceryl laurate, glyceryl linoleate, glyceryl linolenate, glyceryl myristate, glyceryl oleate, and glyceryl palmitate; diglycerides, for example, glyceryl diisopalmitate, glyceryl diisostearate, glyceryl dilaurate, glyceryl dilinoleate, glyceryl dimyristate, glyceryl dioleate, glyceryl dipalmitate, and glyceryl distearate; triglycerides, for example $C_{10}$-$C_{16}$ triglycerides, $C_{18}$-$C_{36}$ triglycerides, and coco triglycerides; and mixed glycerides, such as glyceryl caprilate/caprate, glyceryl palmitate/lactate, glyceryl palmitate/stearate, glyceryl citrate/stearate, glyceryl stearate/diacetate, glyceryl stearate/lactate, glyceryl stearate/succinate, glyceryl acetate/stearate, glyceryl stearate/malate, glyceryl stearate/maleate, glyceryl cocoate/citrate/lactate, glyceryl ethylhexanate/stearate/adipate, glyceryl isostearate/myristate, glyceryl laurate/oleate, caprilate/caprate/cocoate glycerides, caprilate/caprate/laurate triglycerides, caprilate/caprate/linoleate triglycerides, caprilate/caprate/myristate/stearate triglycerides, caprilate/caprate/stearate triglycerides, caprilate/caprate/succinate triglycerides, oleate/linoleate triglyceride, and dicaprilate/dicaprate glycerides; among others.

Propylene glycol esters, such as propylene glycol dicaprilate/dicaprate, which is a mixed diester of propylene glycol and a combination of $C_8$-$C_{10}$ fatty acids, may also be used as emollients.

"Alkyl esters" refers to compounds that may be obtained by the esterification of an alkanol and an acid, such as alkyl $C_{12}$-$C_{15}$ benzoates; alkyl $C_{12}$-$C_{15}$ lactates; methyl esters, for example methyl caproate, methyl caprilate, methyl cocoate, methyl caprilate/caprate, methyl laurate, methyl linoleate, methyl myristate, methyl oleate, methyl palmate, methyl palmitate, and methyl stearate; ethyl esters, for examples ethyl caprate, ethyl isostearate, ethyl laurate, ethyl linoleate, ethyl linolenate, ethyl myristate, ethyl oleate, ethyl palmate, ethyl palmitate, and ethyl stearate; isopropyl esters, for examples isopropyl isostearate, isopropyl lanolate, isopropyl laurate, isopropyl linoleate, isopropyl myristate, isopropyl oleate, isopropyl palmitate, and isopropyl stearate; butyl ester, for example butyl isostearate, butyl myristate, butyl oleate, and butyl stearate; isobutyl esters, for example isobutyl myristate, isobutyl palmitate, and isobutyl stearate; hexyl esters, for example hexyl isostearate and hexyl laurate; isohexyl esters, for examples isohexyl caprate, isohexyl laurate, isohexyl neopentanoate, and isohexyl palmitate; cetyl esters, for example cetyl ethylhexanoate, cetyl caprilate, cetyl isononanoate, cetyl lactate, cetyl laurate, cetyl myristate, cetyl oleate, cetyl palmitate, cetyl ricinoleate, and cetyl stearate; isocetyl esters, for example isocetyl ethylhexanoate, isocetyl isodecanoate, isocetyl isostearate, isocetyl laurate, isocetyl myristate, isocetyl palmitate, and isocetyl stearate; cetearyl esters for example cetearyl ethylhexanoate, cetearyl isononanoate, cetearyl nonanoate, cetearyl palmate, and cetearyl palmitate; decyl esters, for example decyl castorate, decyl cocoate, decyl isostearate, decyl myristate, decyl oleate, decyl palmitate, and decyl succinate; isodecyl esters, for example isodecyl citrate, isodecyl cocoate, isodecyl ethylhexanoate, isodecyl isononanoate, isodecyl laurate, isodecyl myristate, isodecyl neopentanoate, isodecyl oleate, isodecyl palmitate, and isodecyl stearate; ethylhexyl esters, for example ethylhexyl benzoate, ethylhexyl caprilate/caprate, ethylhexyl cocoate, ethylhexyl ethylhexylhexanoate, ethylhexyl isononanoate, ethylhexyl isopalmitate, ethylhexyl isostearate, ethylhexyl laurate, ethylhexyl myristate, ethylhexyl neopentanoate, ethylhexyl oleate, ethylhexyl palmitate, and ethylhexyl stearate; hexyldecyl esters, for example, hexyldecyl benzoate, hexyldecyl ethylhexanoate, hexyldecyl hexyldecanoate, hexyldecyl laurate, hexyldecyl oleate, and hexyldecyl stearate; isostearyl esters, for example isostearyl acetate, isostearyl benzoate, isostearyl ethylhexanoate, isostearyl isononanoate, isostearyl isostearate, isostearyl lactate, isostearyl laurate, isostearyl linoleate, isostearyl myristate, isostearyl neopentanoate, and isostearyl palmitate; lauryl esters, for example lauryl cocoate, lauryl ethylhexanoate, lauryl isostearate, lauryl lactate, lauryl myristate, lauryl oleate, lauryl palmitate, and lauryl stearate; myristyl esters, for example myristyl acetate, myristyl ethylhexanoate, myristyl isostearate, myristyl lactate, myristyl myristate, myristyl neopentanoate, myristyl propionate, and myristyl stearate; octyldecyl esters, for example octyldecyl benzoate, octyldecyl cocoate, octyldecyl ethylhexanoate, octyldecyl lactate, octyldecyl myristate, octyldecyl neodecanoate, octyldecyl neopentanoate, octyldecyl oleate, and octyldecyl stearate; oleyl esters, for example oleyl acetate, oleyl lactate, oleyl lanolate, oleyl linoleate, oleyl myristate, oleyl oleate, and oleyl stearate; and stearyl esters, for example stearyl acetate, stearyl benzoate, stearyl caprilate, stearyl citrate, stearyl lactate, stearyl linoleate, and stearyl stearate; among others.

The esters may be further linked to polyethylene glycol and/or polypropylene glycol units.

"Alkanes" refers to linear or branched hydrocarbon chains having from 12 to 28 carbon atoms.

"Glycols" refers to "diols" and "polyethylene glycols" as previously defined.

"Ethers" may be selected from, among others, dicaprilyl ether, distearylether, as well as ethers linked to polyethylene glycol and/or polypropylene glycol units, such as, stearyl PPG-15 ether, butyl PPG-14 ether, myristyl PPG-3 ether, among other.

The composition according to the invention may comprise rheological modifiers for increasing or decreasing the viscosity thereof. Rheological modifiers, in the context of the present invention, may be selected from, among others, carbomers, acrylates, celluloses, xanthans, dextrans and mixtures thereof. Examples of rheological modifiers are sodium hydroxyethylacrylate/acryloyldimethyltaurate copolymer, carbomers, acrylates, xanthans, dextrans and celluloses.

"Carbomers" refers to high molecular weight polymers of acrylic acid, they may be homopolymers, and they may also be cross-linked with a pentaerythritol allyl ether, saccharose allyl ether or propylene allyl ether. Examples of carbomers are carbomer, potassium carbomer, sodium carbomer, calcium and potassium carbomer, TEA carbomer and hydroxypropylethylenediamine carbomer, among others.

"Acrylates" or "(meth)acrylates" may be selected from sodium hydroxyethylacrylate/acryloyldimethyltaurate copolymer, acrylates/beheneth-25 methacrylate copolymer, acrylates/$C_{10-30}$-alkylacrylate copolymer, acrylates/ceteth-20 itaconate copolymer, acrylates/ceteth-20 methacrylate copolymer, acrylates/diacetoneacrylamide copolymer, acrylates/laureth-25 methacrylate copolymer, acrylates/methoxy PEG-15 methacrylate copolymer, acrylates/palmeth-25 acrylate copolymer, acrylates/palmeth-25 itaconate copolymer, acrylates/steareth-20 itaconate copolymer, acrylates/steareth-20 methacrylate copolymer, acrylates/steareth-50 acrylate copolymer, methacrylates/stearylmethacrylate copolymer, sodium acrylate/sodium acryloyldimethyltaurate copolymer, sodium acrylate/sodium acryloyldimethyltaurate/acrylamide copolymer, sodium acrylate/vinyl alcohol copolymer, sodium acrylate/vinylacetamide copolymer, sodium acrylates copolymer, sodium acrylates/acrolein copolymer, starch/acrylates/acrylamide copolymer, cross-linked sodium acrylate polymers, cross-linked sodium acrylate/acryloyldimethyltaurate/dimethylacrylamide polymers, and $C_{10}$-$C_{30}$ alkyl polyacrylate, polyacrylates, among others.

"Celluloses" may be selected from cellulose, methylcellulose, ethylcellulose, hydroxypropylmethylcellulose, hydroxypropylcellulose, methylethylcellulose, and microcrystalline cellulose, among others.

"Xanthans" may be selected from xanthan gum, hydroxypropyltrimonium xanthan gum, among others.

"Dextrans" may be selected from dextran, carboxymethyldextran, sodium carboxymethyldextran, and sodium salt dextran sulfate.

The composition according to the invention may comprise perfumes and essential oils, such as any fragrance substance commonly used in the field of cosmetics and lavender, jasmine, rose, eucalyptus, citronella, sandalwood, vetiver, lemon, orange, bergamot, musk essential oils.

The composition according to the invention may comprise preserving agents for preventing the development of microorganisms therein. Preserving agents may be selected from, among other, phenols, phenoxy derivatives, heterocyclic derivatives, tropolone, ethylhexylglycerin, and mixtures thereof. Examples of preserving agents are phenoxyethanol, tropolone, chlorophenesin, ethylhexylglycerin, isothiazolidone, diazolidinylurea and parabens.

"Phenols" and "phenoxy derivatives" may be selected from parabens, such as methylparaben, ethylparaben, propylparaben, isopropylparaben, butylparaben, isobutylparaben, phenylparaben, potassium paraben, potassium methylparaben, potassium ethylparaben, potassium propylparaben, potassium butylparaben, sodium paraben, sodium methylparaben, sodium ethylparaben, sodium propylparaben, sodium isopropylparaben, sodium isobutylparaben, hexamidine diparaben, and hexamidine paraben; phenoxyethanol; phenoxyisopropanol; chlorophenesin; chlorophene; bromochlorophene; triclosan; chloroxylenol; climbazole; isopropylcresol; salicylic acid; calcium salicylate; magnesium salicylate; potassium salicylate; sodium salicylate; salicylate-MEA (salicylic acid and 2-aminoethanol 1:1); salicylate-TEA (salicylic acid and 2,2',2"-nitrilotriethanol 1:1); p-chloro-m-cresol; potassium o-phenylphenate, and sodium o-phenylphenate; among others.

"Heterocyclic derivatives" may be selected from isothiazolinones, such as methylisothiazolinone and methylchloroisothiazolinone; diazolidinylurea; 5-bromo-5-nitro-1,3-dioxane and dimethyloxazolidine; among other.

The composition according to the invention may comprise solvent for dissolving other substances comprised therein. Common solvents in the context of the present invention may be selected from, among other, water, oleyl alcohol, ethoxydiglycol, ethyl alcohol, isopropyl alcohol, benzyl alcohol, and mixtures thereof.

The composition according to the invention may comprise emulsifiers for promoting the formation of intimate mixtures of non-miscible liquids by altering the interfacial tension. Emulsifiers, in the context of the present invention, may be selected from, among others, polysorbates, sorbitan esters, ethoxylated fatty alcohols, and mixtures thereof.

"Polysorbates" refer to PEG-ylated derivatives of sorbitan that are esterified with fatty acids, such as polysorbate 20, polysorbate 21, polysorbate 40, polysorbate 60, polysorbate 61, polysorbate 65, polysorbate 80, polysorbate 81, and polysorbate 85, among others.

"Sorbitan esters" may be selected from sorbitan caprylate, sorbitan cocoate, sorbitan diisostearate, sorbitan dioleate, sorbitan isostearate, sorbitan laurate, sorbitan oleate, sorbitan olivate, sorbitan palmitate, sorbitan sesquiisostearate, sorbitan sesquioleate, sorbitan stearate, sorbitan triisostearate, sorbitan trioleate, sorbitan tristearate, and sorbitan undecylenate, among others.

"Ethoxylated fatty alcohols" may be selected from ethoxylated derivatives of behenyl alcohol, such as beneth-2, beneth-5, beneth-10, beneth-15, beneth-20, beneth-25, and beneth-30, among others; $C_{11-13}$ pareth-10, $C_{11-13}$ pareth-6, $C_{11-13}$ pareth-9, $C_{11-15}$ pareth-12, $C_{11-15}$ pareth-15, $C_{11-15}$ pareth-20, $C_{11-15}$ pareth-3, $C_{11-15}$ pareth-30, $C_{11-15}$ pareth-5, $C_{11-15}$ pareth-7, $C_{11-15}$ pareth-9, $C_{11-21}$ pareth-10, $C_{11-21}$ pareth-3, $C_{12-13}$ pareth-10, $C_{12-13}$, pareth-15, $C_{12-13}$ pareth-2, $C_{12-13}$ pareth-23, $C_{12-13}$ pareth-3, $C_{12-13}$ pareth-4, $C_{12-13}$ pareth-5, $C_{12-13}$ pareth-6, $C_{12-13}$ pareth-7, $C_{12-13}$ pareth-9, $C_{12-14}$ pareth-12, $C_{12-14}$pareth-3, $C_{12-14}$ pareth-7, $C_{12-15}$ pareth-10, $C_{12-15}$ pareth-11, $C_{12-15}$ pareth-12, $C_{12-15}$ pareth-2, $C_{12-15}$ pareth-3, $C_{12-15}$ pareth-4, $C_{12-15}$ pareth-5, $C_{12-15}$ pareth-7, $C_{12-15}$ pareth-9, $C_{12-16}$ pareth-5, $C_{12-16}$ pareth-7, $C_{12-16}$ pareth-9, $C_{14-15}$ pareth-11, $C_{14-15}$ pareth-12, $C_{14-15}$ pareth-13, $C_{14-15}$ pareth-4, $C_{14-15}$ pareth-7, $C_{20-22}$ pareth-30, $C_{20-40}$ pareth-24, $C_{20-40}$ pareth-3, $C_{20-40}$ pareth 40, $C_{22-24}$ pareth-33, $C_{30-50}$ pareth-10, $C_{30-50}$ pareth-3, $C_{30-50}$ pareth-40, $C_{40-60}$ pareth-10, $C_{40-60}$ pareth-3, $C_{9-11}$ pareth-3, $C_{9-11}$ pareth-4, $C_{9-11}$ pareth-6, $C_{9-11}$ pareth-8, $C_{9-15}$ pareth-8; ethoxylated derivatives of cetearyl alcohol, such as ceteareth-10, ceteareth-11, ceteareth-12, ceteareth-13, ceteareth-14, ceteareth-15, ceteareth-16, ceteareth-17, ceteareth-18, ceteareth-2, ceteareth-20, ceteareth-22, ceteareth-23, ceteareth-24, ceteareth-25, ceteareth-27, ceteareth-28, ceteareth-29, ceteareth-3, ceteareth-30, ceteareth-33, ceteareth-34, ceteareth-4, ceteareth-5, ceteareth-50, ceteareth-6, ceteareth-60, ceteareth-7, ceteareth-8, and ceteareth-9, among others; ethoxylated derivatives of cetyl alcohol, such as ceteth-1, ceteth-10, ceteth-12, ceteth-13, ceteth-14, ceteth-15, ceteth-16, ceteth-17, ceteth-18, ceteth-2, ceteth-20, ceteth-23, ceteth-24, ceteth-25, ceteth-3, ceteth-30, ceteth-4, ceteth-5, ceteth-6, and ceteth-7, among others; ethoxylated derivatives of cetoleyl alcohol, such as cetoleth-10, cetoleth-11, cetoleth-15, cetoleth-18, cetoleth-2, cetoleth-20, cetoleth-22, cetoleth-4, cetoleth-5, and cetoleth-6, among others; ethoxylated derivatives of decanol, such as deceth-10, deceth-3, deceth-4, deceth-5, deceth-6, deceth-7, deceth-8, and deceth-9, among others; ethoxylated derivatives of lauryl alcohol, such as laureth-1, laureth-10, laureth-11, laureth-13, laureth-14, laureth-15, laureth-16, laureth-2, laureth-20, laureth-23, laureth-25, laureth-3, laureth-30, laureth-4, laureth-6, laureth-7, laureth-8, and laureth-9, among others; ethoxylated derivatives of myristyl alcohol, such as myreth-10, myreth-2, myreth-3, myreth-4, and myreth-5, among others; ethoxylated derivatives of oleyl alcohol, such as oleth-10, oleth-11, oleth-12, oleth-15, oleth-16, oleth-2, oleth-3, oleth-30, oleth-35, oleth-4, oleth-40, oleth-45, oleth-5, oleth-6, oleth-7, oleth-8, and oleth-9, among others; and ethoxylated derivatives of stearyl alcohol such as steareth-1, steareth-10, steareth-11, steareth-13, steareth-14, steareth-15, steareth-16, steareth-2, steareth-20, steareth-200, steareth-21, steareth-25, steareth-3, steareth-4, steareth-5, steareth-6, steareth-7, and steareth-8, among others.

The composition according to the invention may comprise silicones such as aminoethylaminopropyl dimethicone, aminopropyl dimethicone, behenyl dimethicone, bis(aminopropyl)dimethicone, bis(hydroxyethoxypropyl)dimethicone, bis(mercaptopropyl)dimethicone, bis-PEG(1-20)dimethicone, $C_{20-24}$ alkyl dimethicone, $C_{24-28}$ alkyl dimethicone, cetyl dimethicone, diphenyl dimethicone, diphenylisopropyl dimethicone, hexyl dimethicone, hydroxypropyl dimethicone, stearyl dimethicone, vinyl dimethicone, $C_{24-28}$ alkyl methicone, $C_{26-28}$ alkyl methicone, $C_{30-45}$ alkyl methicone, stearyl methicone, among others.

The composition according to the invention may comprise antioxidants for inhibiting reactions promoted by oxygen, thus avoiding oxidation and rancidity of the composition. Common oxidants in the context of the present invention may be selected from, among others, vitamins C and E and derivatives thereof, such as tocopherol (vitamin E), ascorbic acid (vitamin C), and ascorbyl palmitate, among others; as well as weak organic acids, such as citric acid, among others.

The composition according to the present invention may comprise chelating agents such as 2,6-dicarboxypyridine; EDTA (ethylendiaminotetraacetic acid) and its salt, such as the calcium disodium salt, diammonium salt, dipotassium salt, disodium salt; cyclodextrin; oxalic acid and its derivatives, such as dimethyl oxalate, diethyl oxalate, dibutyl oxalate, diisobutyl oxalate, diisopropyl oxalate, dilithium oxalate, dipotassium oxalate, disodium oxalate; citric acid and its derivatives, such as acetyltrihexyl citrate, potassium citrate, among others.

The composition according to the invention may comprise vitamins such as vitamins A, C, D, and E.

In a preferred embodiment, the composition according to the invention comprises, in addition to the compound of formula (I), a compound of formula (II):

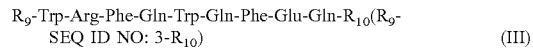

$R_5$-Arg-Gly-Asp-Gly-Pro-Gln-Gly-Pro-Gln-$R_6$($R_5$-SEQ ID NO: 2-$R_6$)     (II)

wherein
$R_5$ is selected from the group consisting of H, $C_1$-$C_{24}$ alkyloyl, $C_2$-$C_{24}$ alkenyloyl, and $C_6$-$C_{10}$ aryl;
$R_6$ is selected from the group consisting of —$OR_7$, —$SR_7$, —$NR_7R_8$, and a polymer derived from polyethylene glycol;
$R_7$ and $R_8$ are independently selected from the group consisting of H; $C_1$-$C_6$ alkyl; $C_3$-$C_8$ cycloalkyl; $C_6$-$C_{10}$ aryl; $C_6$-$C_{10}$ aryl-$C_1$-$C_6$ alkyl; 5, 6 or 7 membered heterocycle containing 1, 2 or 3 heteroatoms in the ring independently selected from the group consisting of N, O and S; 5 or 6 membered monocyclic heteroaryl containing 1, 2, 3 or 4 heteroatoms in the ring independently selected from the group consisting of N, O and S; 8, 9 or 10 membered bicyclic heteroaryl containing 1, 2, 3 or 4 heteroatoms independently selected from the group consisting of N, O and S; heteroaryl-$C_1$-$C_3$ alkyl, wherein the heteroaryl is monocyclic or bicyclic as previously defined, its stereoisomers, its cosmetically acceptable salts, or mixtures thereof.

Preferably $R_5$ is selected from the group consisting of H, $C_{10}$-$C_{24}$ alkyloyl and $C_{10}$-$C_{24}$ alkenyloyl; more preferably from the group consisting of caproyl ($CH_3$—$(CH_2)_8$—C(O)—), lauroyl ($CH_3$—$(CH_2)_{10}$—C(O)—), myristoyl ($CH_3$—$(CH_2)_{12}$—C(O)—), palmitoyl ($CH_3$—$(CH_2)_{14}$—C(O)—), stearoyl ($CH_3$—$(CH_2)_{16}$—C(O)—), arachidoyl ($CH_3$—$(CH_2)_{18}$—C(O)—) and behenoyl ($CH_3$—$(CH_2)_{20}$—C(O)—); still more preferably, $R_5$ is palmitoyl.

Preferably $R_6$ is selected from the group consisting of —$OR_7$, —$SR_7$, —$NR_7R_8$, wherein $R_7$ and $R_8$ are independently selected from the group consisting of H and $C_1$-$C_6$ alkyl; more preferably $R_6$ is selected from the group consisting of —OH, —SH, —$NH_2$; still more preferably $R_6$ is —$NH_2$.

In a more preferred embodiment, $R_5$ is palmitoyl and $R_6$ is —$NH_2$ i.e., the compound of formula (II) is a peptide having the sequence Palm-RGDGPQGPQ-$NH_2$ (Palm-SEQ ID NO: 2—$NH_2$).

In another preferred embodiment, the composition according to the invention comprises, in addition to the compound of formula (I) and optionally the compound of formula (II), a compound of formula (III):

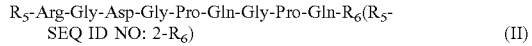

$R_9$-Trp-Arg-Phe-Gln-Trp-Gln-Phe-Glu-Gln-$R_{10}$($R_9$-SEQ ID NO: 3-$R_{10}$)     (III)

wherein
$R_9$ is selected from the group consisting of H, $C_1$-$C_{24}$ alkyloyl, $C_2$-$C_{24}$ alkenyloyl, and $C_6$-$C_{10}$ aryl;
$R_{10}$ is selected from the group consisting of —$OR_{11}$, —$SR_{11}$, —$NR_{11}R_{12}$, and a polymer derived from polyethylene glycol;
$R_{11}$ and $R_{12}$ are independently selected from the group consisting of H; $C_1$-$C_6$ alkyl; $C_3$-$C_8$ cycloalkyl; $C_6$-$C_{10}$ aryl; $C_6$-$C_{10}$ aryl-$C_1$-$C_6$ alkyl; 5, 6 or 7 membered heterocycle containing 1, 2 or 3 heteroatoms in the ring independently selected from the group consisting of N, O and S; 5 or 6 membered monocyclic heteroaryl containing 1, 2, 3 or 4 heteroatoms in the ring independently selected from the group consisting of N, O and S; 8, 9 or 10 membered bicyclic heteroaryl containing 1, 2, 3 or 4 heteroatoms independently selected from the group consisting of N, O and S; heteroaryl-$C_1$-$C_3$ alkyl, wherein the heteroaryl is monocyclic or bicyclic as previously defined, its stereoisomers, its cosmetically acceptable salts, or mixtures thereof.

Preferably $R_9$ is selected from the group consisting of H, $C_{10}$-$C_{24}$ alkyloyl and $C_{10}$-$C_{24}$ alkenyloyl; more preferably from the group consisting of caproyl ($CH_3$—$(CH_2)_8$—C(O)—), lauroyl ($CH_3$—$(CH_2)_{10}$—C(O)—), myristoyl ($CH_3$—$(CH_2)_{12}$—C(O)—), palmitoyl ($CH_3$—$(CH_2)_{14}$—C(O)—), stearoyl ($CH_3$—$(CH_2)_{16}$—C(O)—), arachidoyl ($CH_3$—$(CH_2)_{18}$—C(O)—) and behenoyl ($CH_3$—$(CH_2)_{20}$—C(O)—); still more preferably, $R_9$ is palmitoyl.

Preferably $R_{10}$ is selected from the group consisting of —$OR_{11}$, —$SR_{11}$, —$NR_{11}R_{12}$, wherein $R_{11}$ and $R_{12}$ are independently selected from the group consisting of H and $C_1$-$C_6$ alkyl; more preferably $R_{10}$ is selected from the group consisting of —OH, —SH, —$NH_2$; still more preferably $R_{10}$ is $NH_2$.

In a more preferred embodiment, $R_9$ is palmitoyl and $R_{10}$ is —$NH_2$, the compound of formula (III) is a peptide having the sequence Palm-WRFQWQFEQ-$CONH_2$ (Palm-SEQ ID NO: 3-$NH_2$).

In a particular embodiment, the composition according to the invention comprises a compound of formula (I) and a compound of formula (II), wherein $R_1$ and $R_5$ are independently selected form the group consisting of $C_{10}$-$C_{24}$ alkyloyl and $C_{10}$-$C_{24}$ alkenyloyl; more preferably from the group consisting of caproyl ($CH_3$—($CH_2$)$_8$—C(O)—), lauroyl ($CH_3$—($CH_2$)$_{10}$—C(O)—), myristoyl ($CH_3$—($CH_2$)$_{12}$—C(O)—), palmitoyl ($CH_3$—($CH_2$)$_{14}$—C(O)—), stearoyl ($CH_3$—($CH_2$)$_{16}$—C(O)—), arachidoyl ($CH_3$—($CH_2$)$_{18}$—C(O)—) and behenoyl ($CH_3$—($CH_2$)$_{20}$—C(O)—); still more preferably $R_1$ and $R_5$ are palmitoyl; and wherein $R_2$ and $R_6$ are independently selected from the group consisting of —$OR_3$, —$SR_3$, —$NR_3R_4$, wherein $R_3$ and $R_4$ are independently selected from the group consisting of H and $C_1$-$C_6$ alkyl; more preferably $R_2$ and $R_6$ are independently selected from the group consisting of —OH, —SH, —$NH_2$; still more preferably $R_2$ and $R_6$ are $NH_2$.

In another particular embodiment, the composition according to the invention comprises a compound of formula (I) and a compound of formula (II), wherein $R_1$ and $R_5$ are palmitoyl and wherein $R_2$ and $R_6$ are —$NH_2$, i.e., the composition comprises a peptide having the sequence Palm-SEQ ID NO: 1-$NH_2$ and a peptide having the sequence Palm-SEQ ID NO: 2-$NH_2$.

In another particular embodiment, the composition according to the invention comprises a compound of formula (I) and a compound of formula (III), wherein $R_1$ and $R_9$ are independently selected from the group consisting of H, $C_{10}$-$C_{24}$ alkyloyl and $C_{10}$-$C_{24}$ alkenyloyl; more preferably from the group consisting of caproyl ($CH_3$—($CH_2$)$_8$—C(O)—), lauroyl ($CH_3$—($CH_2$)$_{10}$—C(O)—), myristoyl ($CH_3$—($CH_2$)$_{12}$—C(O)—), palmitoyl ($CH_3$—($CH_2$)$_{14}$—C(O)—), stearoyl ($CH_3$—($CH_2$)$_{16}$—C(O)—), arachidoyl ($CH_3$—($CH_2$)$_{18}$—C(O)—) and behenoyl ($CH_3$—($CH_2$)$_{20}$—C(O)—); still more preferably $R_1$ and $R_9$ are palmitoyl; and wherein $R_2$ and $R_{10}$ are independently selected form the group consisting of —$OR_3$, —$SR_3$, —$NR_3R_4$, wherein $R_3$ and $R_4$ are independently selected from the group consisting of H and $C_1$-$C_6$ alkyl; more preferably $R_2$ and $R_{10}$ are independently selected from the group consisting of —OH, —SH, —$NH_2$; still more preferably $R_2$ and $R_{10}$ are $NH_2$.

In another particular embodiment, the composition according to the invention comprises a compound of formula (I) and a compound of formula (III), wherein $R_1$ and $R_9$ are palmitoyl, and wherein $R_2$ and $R_{10}$ are —$NH_2$, i.e., the composition comprises a peptide having the sequence Palm-SEQ ID NO: 1-$NH_2$ and a peptide having the sequence Palm-SEQ ID NO: 3-$NH_2$.

In another particular embodiment, the composition according to the invention comprises a compound of formula (I), a compound of formula (II), and a compound of formula (III), wherein $R_1$, $R_5$ and $R_9$ are independently selected from the group consisting of H, $C_{10}$-$C_{24}$ alkyloyl and $C_{10}$-$C_{24}$ alkenyloyl; more preferably from the group consisting of caproyl ($CH_3$—($CH_2$)$_8$—C(O)—), lauroyl ($CH_3$—($CH_2$)$_{10}$—C(O)—), myristoyl ($CH_3$—($CH_2$)$_{12}$—C(O)—), palmitoyl ($CH_3$—($CH_2$)$_{14}$—C(O)—), stearoyl ($CH_3$—($CH_2$)$_{16}$—C(O)—), arachidoyl ($CH_3$—($CH_2$)$_{18}$—C(O)—) and behenoyl ($CH_3$—($CH_2$)$_{20}$—C(O)—); still more preferably $R_1$, $R_5$ and $R_9$ are palmitoyl; and wherein $R_2$, $R_6$ and $R_{10}$ are independently selected from the group consisting of —$OR_3$, —$SR_3$, —$NR_3R_4$, wherein $R_3$ and $R_4$ are independently selected form the group consisting of H and $C_1$-$C_6$ alkyl; more preferably $R_2$, $R_6$ and $R_{10}$ are independently selected from the group consisting of —OH, —SH, —$NH_2$; still more preferably $R_2$, $R_6$ and $R_{10}$ are $NH_2$.

In another particular embodiment, the composition according to the invention comprises a compound of formula (I), a compound of formula (II), and a compound of formula (III), wherein $R_1$, $R_5$ and $R_9$ are palmitoyl, and wherein $R_2$, $R_6$ and $R_{10}$ are —$NH_2$, i.e., the composition comprises a peptide having the sequence Palm-SEQ ID NO: 1-$NH_2$, a peptide having the sequence Palm-SEQ ID NO: 2-$NH_2$, and a peptide having the sequence Palm-SEQ ID NO: 3-$NH_2$.

In a particular embodiment, the compound(s) of formula(s) (I), (II) and/or (III) represent from 0.0001% to 5% by weight with respect to the total weight of the composition.

In a particular embodiment, the composition of the invention comprises:
  compound(s) of formula (I), (II) and/or (III) from 1% to 5% by weight, with respect to the total weight of the composition,
  preserving agents from 0% to 5%,
  vitamins from 0% to 20%,
  solvents, rheological modifiers, emollients, emulsifiers and silicones from 0% to 20%,
  perfumes and essential oils from 0% to 2%, and
  antioxidants and chelating agents from 0% to 5%.

In another preferred embodiment, the compound(s) of formula(s) (I), (II) and/or (III) is(are) incorporated into a cosmetically acceptable vehicle or sustained release system selected from the group consisting of liposomes, millicapsules, microcapsules, nanocapsules, sponges, vesicles, micelles, millispheres, microspheres, nanospheres, microemulsions, nanoemulsions, milliparticles, microparticles, nanoparticles, and solid lipid nanoparticles, they are incorporated into hydrolyzed vegetal, animal or synthetic proteins, or are adsorbed onto a cosmetically acceptable solid support selected from the group consisting of talc, bentonite, silica, starch and maltodextrin, dextran and its derivatives.

"Sustained release" refers to a delivery system of a compound which provides the gradual release of said compound during a period of time and preferably, although not necessarily, with relatively constant compound release levels over a long period of time. Examples of delivery or sustained release systems are liposomes, millicapsules, microcapsules, nanocapsules, sponges, vesicles, micelles, millispheres, microspheres, nanospheres, microemulsions, nanoemulsions, milliparticles, microparticles, nanoparticles, and solid lipid nanoparticles.

The prefix "milli" refers to structures having a size comprised between 1 mm and 1000 mm. The prefix "micro" refers to structures having a size comprised between 1 µm and 1000 µm. The prefix "nano" refers to structures having a size comprised between 1 nm and 1000 nm.

"Vesicle" refers to a system that is formed naturally comprising a bilayered phospholipid membrane which contains a hydrophilic part and a hydrophobic part. If the vesicle is prepared artificially it is known as a "liposome".

The term "capsules" in combination with any of the previously defined prefixes refers to capsules made of biodegradable polymers, wherein biodegradable polymers are dextran, polylactide and polyglycolic, chondroitin sulfate, polyesters, polyethylene glycols, polycarbonates, polyvinyl alcohols, polyacrylamides, polyamides, polyacrylates, polyetheresters, polymethacrylates, polyurethanes, polycaprolactone, polyphophazenes, polyorthoesters, polyglycolide, copolymers of lysine and lactic acid, and copolymers of lysine-RGD and lactic acid, and the like, and copolymers of the same.

"Sponge" refers to microsponge Delivery System as technology for the controlled release of topical agents and consists of macroporous beads, typically 10-25 microns in diameter, loaded with active agent which is described for example in Embil K. et al J Microencapsul. 1996 September-October; 13(5):575-88.

"Micelle" refers to an aggregate of molecules comprising a polar region (hydrophilic) and an apolar region (hydrophobic), wherein the polar heads are grouped in contact with a surrounding aqueous solvent to form a hydrophilic layer, and the hydrophobic tails locate in the micelle center.

The terms milli-, micro-, and nanoparticles refer to particles whose size is defined according to the prefix milli-, micro, and nano-, as defined above. Said particles may be made of different materials such as glass, polymers (polyethylene, polystyrene), and ceramic materials.

The terms milli-, micro-, and nanospheres refer to spherical particles whose size is defined according to the prefix milli-, micro, and nano-, as defined above. Said spheres may be made of different materials such as glass, polymers (polyethylene, polystyrene), and ceramic materials.

The terms , micro- and nanoemulsion refer to a homogeneous system that is formed by immiscible liquids (or liquids and particles), wherein one type of liquid or particles (dispersed phase) is dispersed in the other liquid(s) (continuous phase), and wherein the prefix micro- or nano-, as defined above, refer to the size of the dispersed phase.

Examples of hydrolyzed vegetal, animal or synthetic proteins are hydrolyzed wheat, oat, barley, corn, soy, bovine seroalbumin, silk, rice, milk, egg white, gelatin, among others.

In another preferred embodiment, the composition according to the invention is provided as a formulation selected from the group consisting of creams, emulsions, oils, milks, balsams, foams, lotions, gels, liniments, serums, soaps, shampoos, ointments, mousses, pomades, powders, bars, pencils, vaporizers, sprays, capsules, tablets, granules, chewing gums, solutions, suspensions, syrups, jellies and gelatins; or incorporated into a fabric selected from the group consisting of bandages, gauzes, t-shirts, tights, socks, underwear, girdles, gloves, diapers, sanitary napkins, dressings, bedspreads, wipes, hydrogels, adhesive patches, non-adhesive patches, and face masks.

In the third aspect, the invention refers to the use of a compound of formula (I), as previously defined, or of a composition, as previously defined, for the cosmetic non-therapeutic treatments and/or care of skin and/or hair; preferably, wherein the cosmetic non-therapeutic treatment and/or care of skin and/or hair is treatment and/or prevention of ageing and hair loss; more preferably, wherein the treatment and/or prevention of ageing is selected from the group consisting of the treatment and/or prevention of wrinkles, fine lines, furrows, irregularities or roughness increase in the size of pores, loss of elasticity, loss of firmness, loss of smoothness, loss of the capacity to recover from deformation, sagging of the skin, appearance of bags under the eyes or the appearance of a double chin, changes to the color of the skin, circles, bags under the eyes, hair loss, and loss of the structure of collagen.

The previous aspect may be also formulated as a method of cosmetic non-therapeutic treatment and/or care of skin and/or hair which comprises applying to the skin and/or hair a compound of formula (I) as previously defined, or of a composition, as previously defined; preferably, wherein the cosmetic non-therapeutic treatment and/or care of skin and/or hair is treatment and/or prevention of ageing and/or hair loss; more preferably, wherein the treatment and/or prevention of ageing is selected from the group consisting of treatment and/or prevention of wrinkles, fine lines, furrows, irregularities or roughness, increase in the size of pores, loss of elasticity, loss of firmness, loss of smoothness, loss of the capacity to recover from deformation, sagging of the skin, appearance of bags under the eyes or the appearance of a double chin, changes to the color of the skin, circles, bags under the eyes, hair loss, and loss of the structure of collagen.

In the fourth aspect, the invention refers to the use of a compound of formula (I), as previously defined, or of a composition, as previously defined, for inducing the formation of collagen.

The following examples are only illustrative and should not be considered as limiting the scope of the invention.

EXAMPLES

Example 1

Solid-phase Synthesis of Compounds of Formula (I), (II) and (II) wherein $R_1$, $R_5$ and $R_9$ are Palmitoyl and $R_2$, $R_6$ and $R_{10}$ are $NH_2$ (Peptides 1-3)

Compounds of formula (I), (II) and (III), peptides 1, 2 and 3, respectively, were synthesized using the solid-phase methodology and the 9-fluorenylmethoxycarbonyl/tert-butyl (Fmoc/t-Bu) strategy. The peptides were synthesized on a 4-methylbenzhydrylamine (MBHA) resin (1.00 g, 0.65 mmol/g) in a 20 mL syringe with a disc-shaped polyethylene filter. The Fmoc-amino acids (Fmoc-aa) are incorporated after removing the Fmoc-protecting group (deprotection was performed with two treatments of 10 minutes each with 20% piperidine in DMF with an amount of 5 mL/g resin) at room temperature. The couplings were performed with Fmoc-aa-COOH (4 equiv), 1-hydroxy-7-azabenzotriazole (HOAt) (4 equiv) and N,N'-diisopropylcarbodiimide (DIPCDI) (4 equiv) in N,N-dimethylformamide (DMF) for 2 hours. The coupling efficiency was followed using the ninhydrin or Clercq or chloranil method according to the corresponding amino acid. Re-coupling was carried out when necessary under stronger conditions using N-[(dimethylamino)-1H-1, 2,3-triazolo[4,5-b]pyridin-1-ylmethylene]-N-methylmethanaminium hexafluorophosphate N-oxide (HATU) (4 equiv) and N,N-ethyldiisopropylamine (DIEA) (8 equiv) for 1 hour or with benzotriazol-1-yloxytris(pyrrolidino)phosphonium hexafluorophosphate (PyBOP) (4 equiv), HOAt (4 equiv) and DIEA (12 equiv) for 2 hours. After coupling the last amino acid, the peptide was acetylated with palmitic acid in the presence of DIPCDI and 1-benzotriazole (HOBt) (3:3:3, in DMF/dichloromethane (DCM) overnight). The final peptide was cleaved from the resin using a mixture of 95% trifluoroacetic acid (TFA), 2.5% triisopropylsilane (TIS) and 2.5% water (10 mL/g resin) for 1 hour. The peptide was precipitated with cold tert-butyl ether. The precipitate was separated by centrifugation at 5000 ppm for 5 minutes. Finally, the peptides were dissolved in water and lyophilized.

The peptides were characterized by reversed phase high performance liquid chromatography (RP-HPLC) in a Waters series 996 photodiode detector. This instrument was provided with a Waters 2695 modular separator and the Millenium program. The reversed phase column used was C18 column (symmetry C18 reversed phase HPLC columns, 4.6×150 mm, 5 µm) (Waters, Ireland). The peptides were detected at 220 nm, and a linear gradient of 5 to 100% acetonitrile (+0.036% TFA) and water (+0.045% TFA) was used for 8 minutes at a flow rate of 1.0 mL/min. The peptides were analyzed by matrix-assisted laser desorption/ionization mass spectroscopy and time-of-flight (MALDI-TOF) analysis, using a matrix of 2,5-dihydroxybenzoic acid (DHB) and a Micromass VG-quattro spectrometer. The peptides had a purity greater than 80% using RP-HPLC.

That indirectly proves the application of the mixture of these peptides object of this invention as anti-wrinkle products.

TABLE 1

Characterization of the peptides synthesized using RP-HPLC and HPLC-MS or MALDI-TOF. The exact mass was calculated using ChemDraw.

| # | Sequence | Retention time (RP-HPLC) (min) | Purity (RP-HPLC) (%) | Theoretical molecular weight (g/mol) | Experimental molecular weight (m + H/z) |
|---|---|---|---|---|---|
| Peptide 1 | Palm-RGDGANPNAAG-NH$_2$ (Palm-SEQ ID NO: 1-NH$_2$) | 6.78 | 92.80 | 1235.70 | 1236.45 |
| Peptide 2 | Palm-RGDGPQGPQ-NH$_2$ (Palm-SEQ ID NO: 2-NH$_2$) | 7.45 | 97.82 | 1147.67 | 1148.54 |
| Peptide 3 | Palm-WRFQWQFEQ-NH$_2$ (Palm-SEQ ID NO: 3-NH$_2$) | 4.16 | 95.19 | 1576.86 | 1577.32 |

Peptide 1 (Palm-RGDGANPNAAG-NH$_2$, Palm-SEQ ID No: 1-NH$_2$) was synthesized using the solid-phase methodology and the Fmoc/t-Bu strategy described above and was obtained in a yield of 67% and a purity greater than 90%.

Peptide 2 (Palm-RGDGPQGPQ-NH$_2$, Palm-SEQ ID NO: 2-NH$_2$) was synthesized using the solid-phase methodology and the Fmoc/t-Bu strategy described above and was obtained in a yield of 73% and a purity greater than 97%.

Peptide 3 (Palm-WRFQWQFEQ-NH$_2$, Palm-SEQ ID NO: 3-NH$_2$) was synthesized using the solid-phase methodology and the Fmoc/t-Bu strategy described above and was obtained in a yield of 73% and a purity greater than 95%.

Example 2

Cell Multiplication and Amplification Using Compounds of Formula (I), (II) and (II) wherein $R_1$, $R_5$ and $R_9$ are Palmitoyl and $R_2$, $R_6$ and $R_{10}$ are NH$_2$ (Peptides 1-3)

The mixture of three peptides 1-3 synthesized in Example 1 were studied in vitro to demonstrate their capacity to increase the number of cells and therefore to indirectly demonstrate their anti-wrinkle capacity. Therefore, the HeLa cells were cultured in DMEM (Dubelcco's modified eagle medium) with low glucose content, containing 10% fetal bovine serum, 5% ultraglutamine, 2.5% penicillin, and 2.5% streptomycin at 37° C. in an incubator with controlled CO$_2$ atmosphere. 96-well plates (Nalge Nunc) were previously coated with 100 ug of the mixture of the three peptides 1-3 synthesized in Example 1, proportion was 1:1:1 in weight and peptide-free wells were used as an experimental control. HeLa cells were seeded at 1×10$^3$ cells/cm$^2$ in the 96-well plates and cultured for 2 and 4 days. The final percentage of cell proliferation was determined with respect to the initial value of the cells treated and not treated with peptides.

This experiment demonstrates the population growth in the number of cells which is enhanced by the presence of the mixture of peptides of the present invention. The cell population also increased significantly with days (FIG. 1).

Example 3

Tests of the Affinity for Fibroblasts Using Compounds of Formula (I), (II) and (II) wherein $R_1$, $R_5$ and $R_9$ are Palmitoyl and $R_2$, $R_6$ and $R_{10}$ are NH$_2$ (Peptides of 1-3)

Human Dermal Fibroblasts (ATCC PCS-201-012) were used for studying their affinity for the mixture 1:1:1 w/w/w of the three peptides 1-3 synthesized in Example 1. The binding of the peptides to the fibroblast cells was therefore studied in Dulbecco's Modified Eagle Medium (DMEM) culture medium at different concentrations in DMEM of the fluoresceine-labeled peptides 1-3 (5 ug/mL, 10 ug/mL, 20 ug/mL and 40 ug/mL, respectively) for 1 hour at room temperature in culture medium. The human dermal fibroblasts treated and not treated with peptides were then washed several times in type V plates at 1500 rpm for 2 minutes to remove the peptides which did not bind to the cells. Next, the treated and untreated cells were analyzed by flow cytometry.

Figure 2:
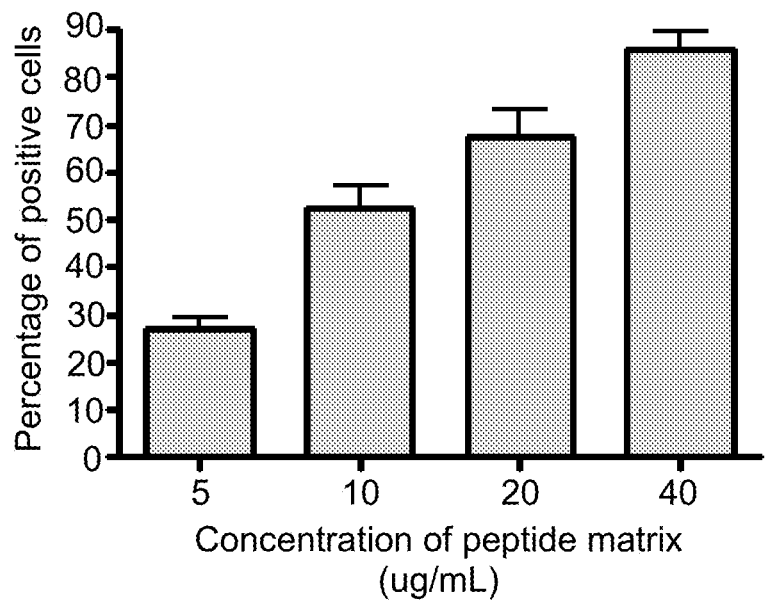
FIG. 2 shows the flow cytometry study of the affinity of the fibroblasts for the mixture of the three peptides 1-3. The results were evaluated after 2 and 4 days of treatment.

This study demonstrates the affinity of the mixture of the three peptides o1-3 for fibroblasts. It also demonstrates a dose-dependent behavior, the cell affinity for the peptide mixture increases as the amount of peptides increases (FIG. 2). That proves the capacity of this mixture of three peptides for binding to the cells, which indicates the application of the mixture of these peptides as potential anti-wrinkle products.

Example 4

Fluorescence Microscopy Study of the Formation of Collagen I and VI for the Mixture of Compounds of Formula (I), (II) and (II) wherein $R_1$, $R_5$ and $R_9$ are Palmitoyl and $R_2$, $R_6$ and $R_{10}$ are NH$_2$ (Peptides 1-3)

Human Dermal Fibroblasts (ATCC PCS-201-012) were seeded at low confluence on a glass material. Twenty-four hours after the seeding, they were treated with a mixture of the three peptides 1-3 synthesized in Example 1, at a concentration of 1.0% w/v in the incubation of the mixture of peptides, each of them being in an equivalent proportion, in weight, in the mixture.

The samples were incubated with the corresponding anti-collagen I and VI antibodies. Antibodies are commercial rabbit polyclonal antibodies against human collagen I or IV: code A03C0377 and A02C0384 provided by Bluegene Biotech Co. Ltd. The untreated cell samples were then analyzed and compared with the treated cells. The equipment used was an Olympus FV1000 spectral confocal microscope.

As can be observed in the preceding images, after the treatment with the mixture of peptides of the present invention, there is a greater fluorescence intensity due to the fact that the signal of collagen I and VI is greater (FIG. 3). This experiment shows the induction of collagens I and VI, which proves the potentials of applying the mixture of these peptides in cosmetics as anti-wrinkle and/or skin stimulating and repairing products.

Example 5

Study of Fibroblast Binding of the Mixture of Compounds of Formula (I), (II) and (II) wherein $R_1$, $R_5$ and $R_9$ are Palmitoyl and $R_2$, $R_6$ and $R_{10}$ are $NH_2$ (Peptides 1-3) by Scanning Electron Microscopy Human dermal fibroblasts were seeded at low confluence on a glass plate 75×25 mm. Twenty-four hours after the seeding, they were treated with a mixture of peptides 1-3 synthesized in Example 1, at a concentration of 1% w/v in DMEM of the mixture of peptides, each of them being in an equivalent proportion, in weight, in the mixture.

The samples were fixed 24 hours after the treatment with glutaraldehyde and successive additions of ethanol at different proportions in water. The untreated cell samples were then analyzed and compared with the treated cells. The equipment used was a filament type field emission scanning electron microscope, model NOVA NANOSEM2.

An increase in the number of filaments which the cell uses for anchoring, as well as an increase in membrane proteins (FIGS. 4A and 4B) can be observed in the scanning electron microscope image of FIG. 4B. This proves the potentials of applying the mixture of these peptides in cosmetics as anti-wrinkle and/or skin stimulating and repairing products.

Example 6

Determination of Collagen Biosynthesis by the Mixture of Compounds of Formula (I), (II) and (II) wherein $R_1$, $R_5$ and $R_9$ are Palmitoyl and $R_2$, $R_6$ and $R_{10}$ are $NH_2$ (Peptides 1-3)

Human Dermal Fibroblasts (ATCC PCS-201-012) (HDFs) were seeded in 96-well plates (3000 cells per well) and left to grow in DMEM containing 5% fetal bovine serum (FBS) for 24 hours. The medium was then replaced with fresh medium containing 0.1% FBS and the corresponding treatment for determining collagen production. After the incubation with the mixture of peptides 1-3 synthesized in Example 1, at a concentration of 1% w/v of the mixture of peptides each of them being in an equivalent proportion, by weigh, in the mixture, for a period of 72 hours, 0.5 ml of supernatant were added to a plate coated with human type I collagen antibody (commercial rabbit polyclonal antibodies against human collagen I, code A03C0377, provided by Bluegene Biotech Co. Ltd). The plate was incubated at room temperature for 2 hours to allow the antibody and the produced collagen to react with one another. The plate was then washed three times with PBS containing 0.5% Tween 20 for removing the remaining unbound sample. Next, a human antibody which recognizes the biotin-labeled type I collagen was added for 1 hour. After washing the plate with phosphate buffered saline (PBS) containing 0.5% Tween 20 for removing non-specific interactions, streptavidin-horseradish peroxidase (HRP) (St Louis, Sigma) was added. The amount of collagen in each well was determined using tetramethylbenzidine (TMB) (St Louis, Sigma) as the substrate for the HRP. The reaction between the HRP and TMB was stopped by adding 1 N HCl, and the O.D. (optical density) was measured at 450 nm. The untreated cells represented the negative control of the experiment. The results were analyzed using a single treatment dose of the peptides 1-3 synthesized in Example 1.

Figure 5:
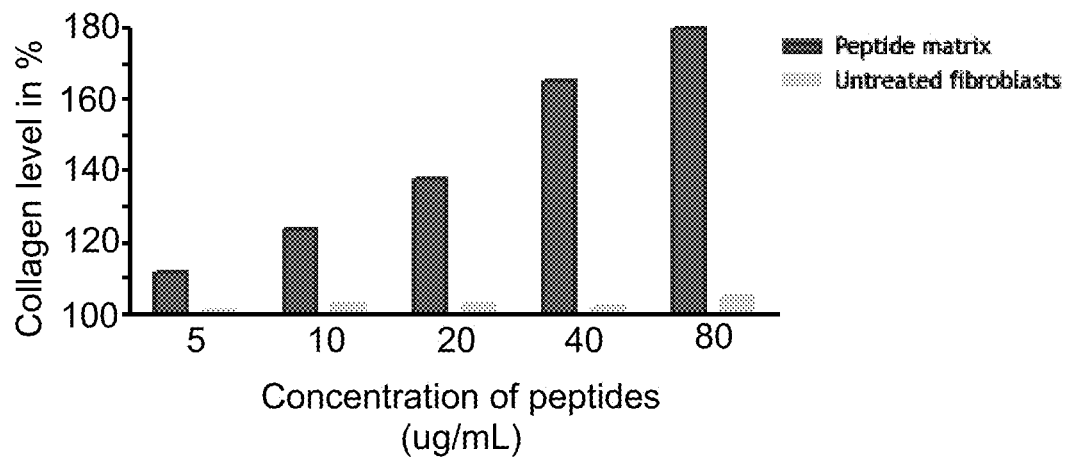
FIG. 5 shows the determination of collagen synthesis in human fibroblasts by the mixture of the three peptides 1-3. This figure shows the induction of type I collagen production by the mixture of peptides 1-3 at different concentrations.

As observed in FIG. 5, the mixture of peptides 1-3 synthesized in Example 1 were capable of inducing type I collagen activation. This proves the application of this mixture of peptides with cosmetic applications as anti-wrinkle and/or skin stimulating and repairing products.

Example 7

Cytotoxic Effect Study of the Mixture of Compounds of Formula (I), (II) and (II) wherein $R_1$, $R_5$ and $R_9$ are Palmitoyl and $R_2$, $R_6$ and $R_{10}$ are $NH_2$ (Peptides of 1-3)

Tested cell lines: 1064SK (CRL-2076), human cell line; skin; morphology: fibroblasts; normal Hs68 (CRL-1635), human cell line; skin; morphology: fibroblasts, HeLa (CCL-2), human cell line; morphology: epithelial.

The isolated cells were cultured in DMEM culture medium supplemented with 10% fetal calf serum and were incubated at 37° for maintenance treatment.

Untreated cells were used as control. The positive control was 0.1% SDS. Cells were seeded at 20.000 cells per well in a 96 well plate. 24 h after seeding the cells were incubated under the conditions described above. After 48 h incubation at 37° C. the culture medium was removed and the MTT reagent was added. Cells incubated 2 h at 37° C. DMSO was then added and the absorbance of the formed formazan salt was measured at 570 nm. Lower absorbance values correspond to cells with lower metabolic activity, which correlates with an increased damage and therefore with an increased cytotoxic effect. Thus the amount of living cells is proportional to the amount of formazan produced. The table 2 shows the IC50 values that mean the concentration that kill 50% of the cell population

TABLE 2

|         | 1064SK      | Hs68       | HeLa       |
|---------|-------------|------------|------------|
| $IC_{50}$ | 1259.67 µM | 991.32 µM  | 858.45 µM  |

As shown in Table 2, the mixture of peptides 1-3 synthesized in Example 1 is not toxic. It only becomes toxic at least to about 858 µM. Therefore, these results mean that the peptides 1-3 synthesized in Example 1 offer a broad window for cosmetic application.

Example 8

In vivo Efficacy: Evaluation of the Anti-wrinkle and Re-densifying Effect of Compounds of Formula (I), (II) and (II) wherein $R_1$, $R_5$ and $R_9$ are Palmitoyl and $R_2$, $R_6$ and $R_{10}$ are $NH_2$ (Peptides 1-3)

The objective of this clinical study was to evaluate if compounds of formula (I), (II) and (II) wherein $R_1$, $R_5$ and $R_9$ are palmitoyl and $R_2$, $R_6$ and $R_{10}$ are $NH_2$, peptides 1-3, have a cosmetic effect, particularly, if the daily use thereof could significantly change the skin parameters such as elasticity, wrinkles, volume, density and firmness. One mixture of peptides 1-3 described above was formulated as a 3% cream.

Ingredients in the cream (the concentrations are expressed as the weigh of each ingredient in 100 g of cream):
ACRYLATES/C10-30 ALKYL ACRYLATE CROSSPOLYMER 0.15%
IMIDAZILIDINYL UREA 0.3%
PROPILENE GLYCOL 2.0%
PHENONIP 0.8%
GLYCERYL STEARATE, PEG-100 STEARATE 6%
CETYL ALCOHOL 0.7%
STEARIC ACID, PALMITIC ACID 1.8%
CAPRYLIC/CAPRIC TRIGLYCERIDES 8.0%
ISOHEXADECANE 3.0%
Mixture of peptides 1-3 (1:1:1 w/w/w) 3%
TRIETHANOLAMINE 0.12%
COLORANT 0.02%
PARFUM 0.1%
DESIONIZED WATER up to 100 g Product was applied once daily (0.1 g/application) in 20 subjects.

Methodology

The elasticity, density and firmness were determined by measuring the skin's capacity to return to its initial state after experiencing deformation under partial vacuum by means of an elastometer. The data were taken with a CUTOMETER® MPA 580 elastometer. The skin elasticity shows the skin's potential capacity to shrink (mm).

Measuring the Wrinkle Thickness

The objective of this study was to evaluate the wrinkle thickness as an additional indicator of skin density and firmness. Data relating to this study was taken with a skinfold caliper. According to its definition, a skinfold caliper measures the thickness of a fold formed by adipose tissue in a specific part of the body and determines its density. In this case, this instrument was only used for measuring the thickness of the cutaneous fold between the eye contour and the temple: an indication in relation to skin compactness is obtained by measuring the changes in the wrinkle. An increase in thickness indicates an increase in skin density and firmness.

Compactness and Elasticity

Figure 6A:
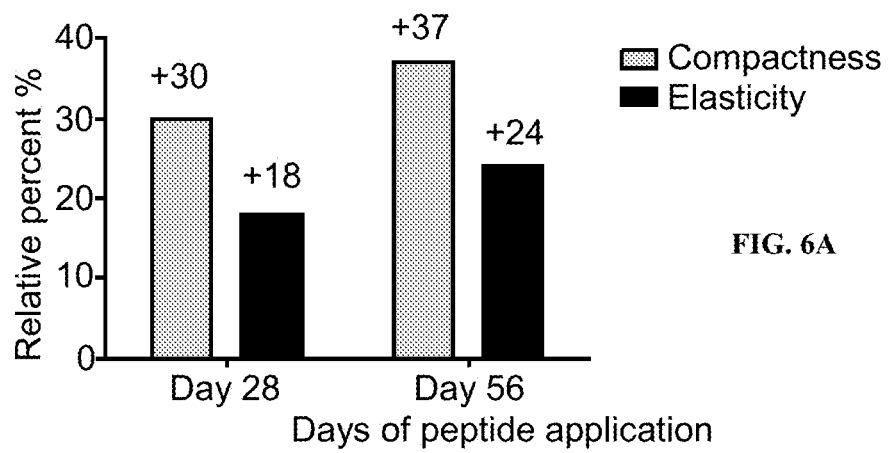
FIG. 6 shows the in vivo analysis of skin elasticity, compactness and wrinkle thickness after applying the mixture of the three peptides 1-3. A, Results of the analysis of skin compactness and elasticity on day 28 and on day 56. B, Results of the analysis of thickness on day 28 and on day 56.

The statistical analysis shows an improvement in skin compactness of 30% and in skin elasticity of 18% on day 28, increasing up to 37% and 24% on day 56, respectively (FIG. 6A). As can be observed from the in vivo study, the mixture of these peptides showed a significant improvement in compactness and elasticity in people who applied the mixture of peptides 1-3 synthesized in Example 1.

Measuring the Wrinkle Thickness

Figure 6B:
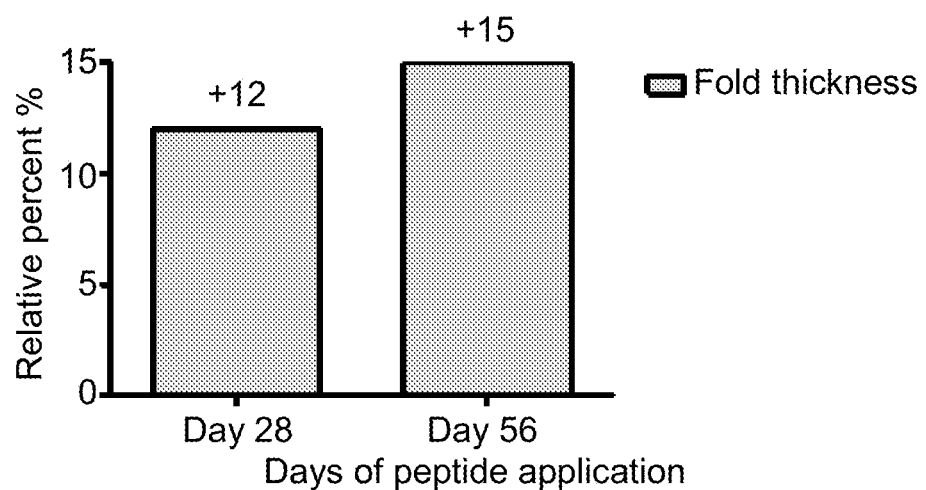

The statistical results show an increase in the volume of fold, 12% on day 28 and 15% on day 56, related to an increase in skin density (FIG. 6B). As observed in this figure, after applying the mixture of peptides 1-3 in a cosmetic formulation, the volume of fold improved significantly, 12% after 28 days of application and 15% after 56 days of application.

Example 9

Hair Dermal Papilla Cell Multiplication and Amplification Using Compounds of Formula (I), (II) and (II) wherein $R_1$, $R_5$ and $R_9$ are Palmitoyl and $R_2$, $R_6$ and $R_{10}$ are $NH_2$ (Peptides 1-3)

Human dermal papilla was isolated from volunteers between 18-50 years of age. The dermal papilla cells were isolated from scalp skin obtained by plastic surgery, these were isolated and cultured in culture plates with 15 mL of culture medium (DMEM, Gibco), adding 10% fetal calf serum (FCS, Gibco), penicillin (50 U/mL)/streptomycin (50 U/mL) at 37° C. under a wet atmosphere of 95% $O_2$ and 5% $CO_2$. The cells were cultured in the presence and absence of a mixture 1:1:1 (w/w/w) of peptides 1-3 synthesized in Example 1.

Figure 7:
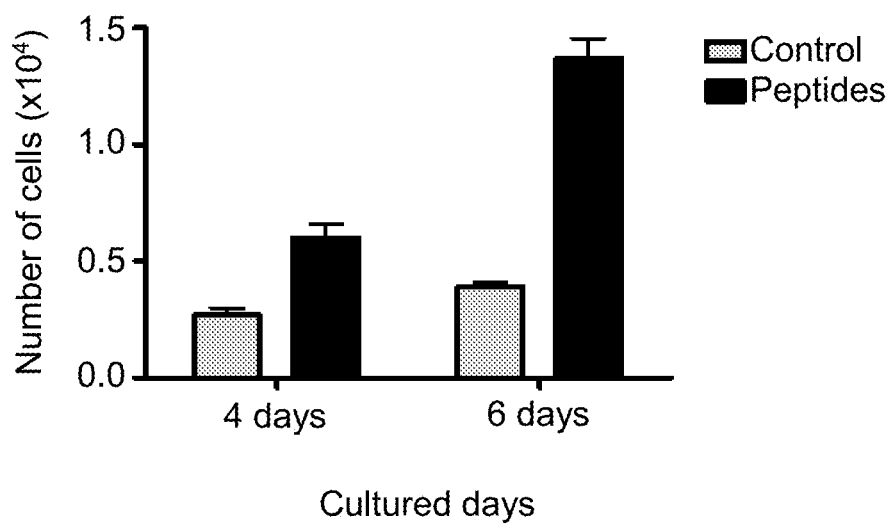
FIG. 7 shows the effect of the mixture of the three peptides 1-3 on human hair dermal papilla cell proliferation. The total cell count was performed after 4 and 6 days of incubation, respectively.

It is demonstrated that by using a mixture of peptides 1-3 synthesized in Example 1, an increase in the human hair dermal papilla cell proliferation is observed after 4 and 6 days, respectively (FIG. 7). This proves the application of this mixture of these peptides with cosmetic applications for use on hair.

Example 10

Determination of Collagen Biosynthesis by Compounds of Formula (I), (II) and (II) wherein $R_1$, $R_5$ and $R_9$ are Palmitoyl and $R_2$, $R_6$ and $R_{10}$ are $NH_2$ (Peptides 1-3)

Human Dermal Fibroblasts (ATCC PCS-201-012) were seeded in 96-well plates (3000 cells per well), and left to grow in DMEM containing 5% fetal bovine serum (FBS) for 48 hours. The medium was then replaced with fresh medium containing 0.1% FBS and the corresponding treatment for determining collagen production. After the incubation with each of the peptides (1, 2, and 3) and the mixture of peptides 1-3 synthesized in Example 1, at different concentrations (20, 40 and 80 µg/ml) of each peptide dissolved in DMEM medium in an equivalent proportion of each of them in the mixture (1:1:1 w/w/w), for a period of 72 hours, the same amounts of supernatant were added to a plate coated with human type I collagen antibody (commercial rabbit polyclonal antibodies against human collagen I, code A03C0377, provided by Bluegene Biotech Co. Ltd). The plate was incubated at room temperature for 2 hours to allow the antibody and the produced collagen to react with one another. The plate was then washed three times with PBS containing 0.5% Tween 20 for removing the remaining unbound sample. Next, a human antibody which recognizes the biotin-labeled type I collagen was added for 1 hour. After washing the plate with phosphate buffered saline (PBS) containing 0.5% Tween 20 for removing non-specific interactions, streptavidin-horseradish peroxidase (HRP) (St Louis, Sigma) was added. The amount of collagen in each well was determined using tetramethylbenzidine (TMB) (St Louis, Sigma) as the substrate for the HRP. The reaction between the HRP and TMB was stopped by adding 1 N HCl, and the O.D. (optical density) was measured at 450 nm. The untreated cells represented the negative control of the experiment.

Figure 8:
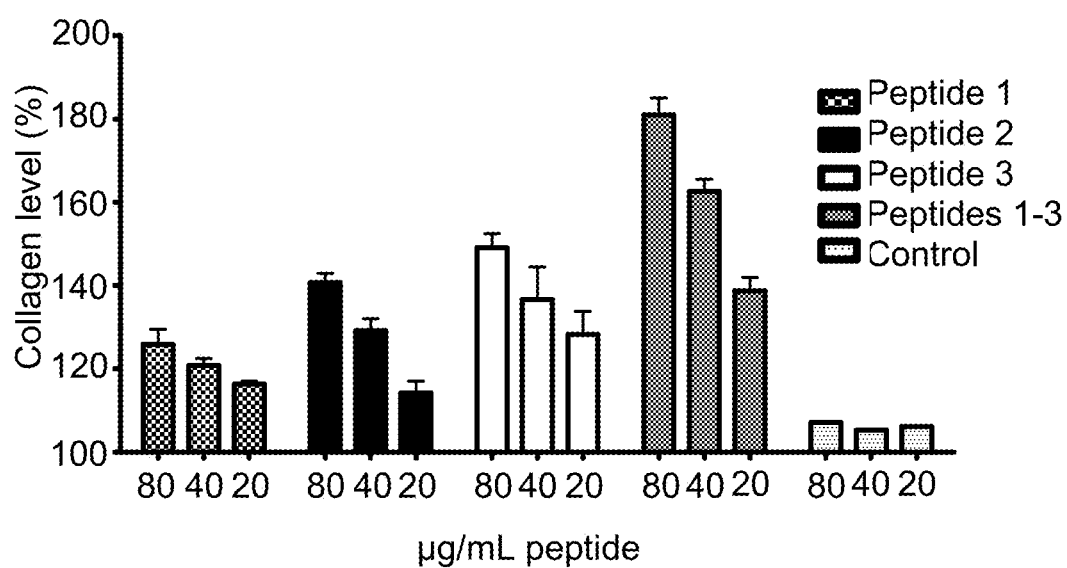
FIG. 8 shows the determination of collagen synthesis in human fibroblasts by each of peptides 1-3 and a mixture thereof. This figure shows the induction of type I collagen production by the peptides 1-3 and a mixture thereof at different concentrations.

As observed in FIG. 8, each of the peptides 1-3 synthesized in Example 1 and the mixture thereof were capable of inducing type I collagen activation. Peptides (1, 2, and 3) were capable of inducing type I collagen production. It can also be observed that the combination of the three peptides in equivalent ratio, by weight, with respect to each of the peptides increased type I collagen production at the different tested concentrations. This proves the application of this mixture of peptides with cosmetic applications as anti-wrinkle and/or skin stimulating and repairing products.

The invention claimed is:

1. A compound of formula (I):

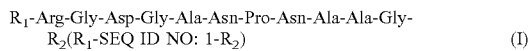

$R_1$-Arg-Gly-Asp-Gly-Ala-Asn-Pro-Asn-Ala-Ala-Gly-$R_2$($R_1$-SEQ ID NO: 1-$R_2$)  (I)

wherein $R_1$ is chosen from the group consisting of H, $C_1$-$C_{24}$ alkyloyl, $C_2$-$C_{24}$ alkenyloyl, and $C_6$-$C_{10}$ aryl;

$R_2$ is chosen from the group consisting of —$OR_3$, —$SR_3$, —$NR_3R_4$, and a polymer derived from polyethylene glycol;

$R_3$ and $R_4$ are independently chosen from the group consisting of H; $C_1$-$C_6$ alkyl; $C_3$-$C_8$ cycloalkyl; $C_6$-$C_{10}$ aryl; $C_6$-$C_{10}$ aryl-$C_1$-$C_6$ alkyl; 5, 6 or 7 membered heterocycle containing 1, 2 or 3 heteroatoms in the heterocyclic ring, wherein the heteroatoms are independently chosen from the group consisting of N, O and S; 5 or 6 membered monocyclic heteroaryl containing 1, 2, 3 or 4 heteroatoms in the heteroaryl ring, wherein the heteroatoms are independently chosen from the group consisting of N, O and S; 8, 9 or 10 membered bicyclic heteroaryl containing 1, 2, 3 or 4 heteroatoms, wherein the heteroatoms are independently chosen from the group consisting of N, O and S; heteroaryl-$C_1$-$C_3$ alkyl, wherein the heteroaryl is monocyclic or bicyclic as previously defined;

its stereoisomers, its cosmetically acceptable salts, or mixtures thereof.

2. The compound according to claim 1, wherein $R_1$ is palmitoyl and $R_2$ is —$NH_2$.

3. A composition which comprises a compound of claim 1 and a cosmetically acceptable excipient.

4. The composition according to claim 3, wherein said composition further comprises a compound of formula (II):

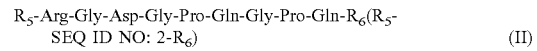

$R_5$-Arg-Gly-Asp-Gly-Pro-Gln-Gly-Pro-Gln-$R_6$($R_5$-SEQ ID NO: 2-$R_6$)  (II)

wherein $R_5$ is chosen from the group consisting of H, $C_1$-$C_{24}$ alkyloyl, $C_2$-$C_{24}$ alkenyloyl, and $C_6$-$C_{10}$ aryl;

$R_6$ is chosen from the group consisting of —$OR_7$, —$SR_7$, —$NR_7R_8$, and a polymer derived from polyethylene glycol;

$R_7$ and $R_8$ are independently chosen from the group consisting of H; $C_1$-$C_6$ alkyl; $C_3$-$C_8$ cycloalkyl; $C_6$-$C_{10}$ aryl; $C_6$-$C_{10}$ aryl-$C_1$-$C_6$ alkyl; 5, 6 or 7 membered heterocycle containing 1, 2 or 3 heteroatoms in the heterocyclic ring, wherein the heteroatoms are independently chosen from the group consisting of N, O and S; 5 or 6 membered monocyclic heteroaryl containing 1, 2, 3 or 4 heteroatoms in the heteroaryl ring, wherein the heteroatoms are independently chosen from the group consisting of N, O and S; 8, 9 or 10 membered bicyclic heteroaryl containing 1, 2, 3 or 4 heteroatoms, wherein the heteroatoms are independently chosen from the group consisting of N, O and S; heteroaryl-$C_1$-$C_3$ alkyl, wherein the heteroaryl is monocyclic or bicyclic as previously defined;

its stereoisomers, its cosmetically acceptable salts, or mixtures thereof.

5. The composition according to claim 4, wherein $R_5$ is palmitoyl and $R_6$ is $NH_2$.

6. The composition according to claim 3, wherein said composition further comprises a compound of formula (III):

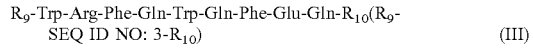

$R_9$-Trp-Arg-Phe-Gln-Trp-Gln-Phe-Glu-Gln-$R_{10}$ ($R_9$-SEQ ID NO: 3-$R_{10}$) (III)

wherein $R_9$ is chosen from the group consisting of H, $C_1$-$C_{24}$ alkyloyl, $C_2$-$C_{24}$ alkenyloyl, and $C_6$-$C_{10}$ aryl;

$R_{10}$ is chosen from the group consisting of —$OR_{11}$, —$SR_{11}$, —$NR_{11}R_{12}$, and a polymer derived from polyethylene glycol;

$R_{11}$ and $R_{12}$ are independently chosen from the group consisting of H; $C_1$-$C_6$ alkyl; $C_3$-$C_8$ cycloalkyl; $C_6$-$C_{10}$ aryl; $C_6$-$C_{10}$ aryl-$C_1$-$C_6$ alkyl; 5, 6 or 7 membered heterocycle containing 1, 2 or 3 heteroatoms in the heterocyclic ring, wherein the heteroatoms are independently chosen from the group consisting of N, O and S; 5 or 6 membered monocyclic heteroaryl containing 1, 2, 3 or 4 heteroatoms in the heteroaryl ring, wherein the heteroatoms are independently chosen from the group consisting of N, O and S; 8, 9 or 10 membered bicyclic heteroaryl containing 1, 2, 3 or 4 heteroatoms, wherein the heteroatoms are independently chosen from the group consisting of N, O and S; heteroaryl-$C_1$-$C_3$ alkyl, wherein the heteroaryl is monocyclic or bicyclic as previously defined;

its stereoisomers, its cosmetically acceptable salts, or mixtures thereof.

7. The composition according to claim 6, wherein $R_9$ is palmitoyl and $R_{10}$ is $NH_2$.

8. The composition according to claim 3, wherein the cosmetically acceptable excipient(s) is chosen from the group consisting of humectants, emollients, rheological modifiers, perfumes, essential oils, preserving agents, solvents, emulsifiers, silicones, antioxidants, chelating agents, vitamins and mixtures thereof.

9. The composition according to claim 3, wherein the total amount of compound of formula (I) represents from 0.0001% to 5% by weight with respect to the total weight of the composition, and the compound of formula (I) is incorporated into a cosmetically acceptable vehicle or sustained release system chosen from the group consisting of liposomes, millicapsules, microcapsules, nanocapsules, sponges, vesicles, micelles, millispheres, microspheres, nanospheres, microemulsions, nanoemulsions, milliparticles, microparticles, nanoparticles, and solid lipid nanoparticles, are incorporated into hydrolyzed vegetal, animal or synthetic proteins, or are adsorbed onto a cosmetically acceptable solid support chosen from the group consisting of talc, bentonite, silica, starch and maltodextrin, dextran and dextran derivatives.

10. The composition according to claim 4, wherein the total amount of compounds of formulas (I) and (II) represents from 0.0001% to 5% by weight with respect to the total weight of the composition, and the compounds of formulas (I) and (II) are incorporated into a cosmetically acceptable vehicle or sustained release system chosen from the group consisting of liposomes, millicapsules, microcapsules, nanocapsules, sponges, vesicles, micelles, millispheres, microspheres, nanospheres, microemulsions, nanoemulsions, milliparticles, microparticles, nanoparticles, and solid lipid nanoparticles, are incorporated into hydrolyzed vegetal, animal or synthetic proteins, or are adsorbed onto a cosmetically acceptable solid support chosen from the group consisting of talc, bentonite, silica, starch and maltodextrin, dextran and dextran derivatives.

11. The composition according to claim 3, wherein said composition is provided in a formulation chosen form the group consisting of creams, emulsions, oils, milks, balsams, foams, lotions, gels, liniments, serums, soaps, shampoos, ointments, mousses, pomades, powders, bars, pencils, vaporizers, sprays, capsules, tablets, granules, chewing gums, solutions, suspensions, syrups, jellies and gelatins; or any of the previous formulations is incorporated into a fabric chosen from the group consisting of bandages, gauzes, t-shirts, tights, socks, underwear, girdles, gloves, diapers, sanitary napkins, dressings, bedspreads, wipes, hydrogels, adhesive patches, non-adhesive patches, and face masks.

12. A method of cosmetic non-therapeutic treatment and/or care of skin and/or hair which comprises topically applying to the skin and/or hair a compound of formula (I) as defined in claim 1.

13. The method according to claim 12, wherein the cosmetic non-therapeutic treatment and/or care of skin and/or hair is treatment of ageing and/or hair loss.

14. The method according to claim 13, wherein the treatment of ageing is chosen from the group consisting of treatment of wrinkles, fine lines, furrows, irregularities or roughness, increase in the size of pores, loss of elasticity, loss of firmness, loss of smoothness, loss of the capacity to recover from deformation, sagging of the skin, appearance of bags under the eyes or the appearance of a double chin, changes to the color of the skin, circles, bags under the eyes, hair loss, and loss of the structure of collagen.

15. A method for inducing the formation of collagen comprising the topical administration of a compound of formula (I) as defined in claim 1.

16. The composition according to claim 6, wherein the total amount of compounds of formulas (I) and (III) represents from 0.0001% to 5% by weight with respect to the total weight of the composition, and the compounds of formulas (I) and (III) are incorporated into a cosmetically acceptable vehicle or sustained release system chosen from the group consisting of liposomes, millicapsules, microcapsules, nanocapsules, sponges, vesicles, micelles, millispheres, microspheres, nanospheres, microemulsions, nanoemulsions, milliparticles, microparticles, nanoparticles, and solid lipid nanoparticles, are incorporated into hydrolyzed vegetal, animal or synthetic proteins, or are adsorbed onto a cosmetically acceptable solid support chosen from the group consisting of talc, bentonite, silica, starch and maltodextrin, dextran and dextran derivatives.

17. The composition according to claim 4, wherein said composition further comprises a compound of formula (III):

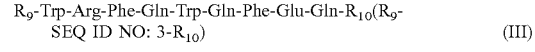

$R_9$-Trp-Arg-Phe-Gln-Trp-Gln-Phe-Glu-Gln-$R_{10}$ ($R_9$-SEQ ID NO: 3-$R_{10}$) (III)

wherein $R_9$ is chosen from the group consisting of H, $C_1$-$C_{24}$ alkyloyl, $C_2$-$C_{24}$ alkenyloyl, and $C_6$-$C_{10}$ aryl;

$R_{10}$ is chosen from the group consisting of —$OR_{11}$, —$SR_{11}$, —$NR_{11}R_{12}$, and a polymer derived from polyethylene glycol;

$R_{11}$ and $R_{12}$ are independently chosen from the group consisting of H; $C_1$-$C_6$ alkyl; $C_3$-$C_8$ cycloalkyl; $C_6$-$C_{10}$ aryl; $C_6$-$C_{10}$ aryl-$C_1$-$C_6$ alkyl; 5, 6 or 7 membered heterocycle containing 1, 2 or 3 heteroatoms in the heterocyclic ring, wherein the heteroatoms are independently chosen from the group consisting of N, O and S; 5 or 6 membered monocyclic heteroaryl containing 1, 2, 3 or 4 heteroatoms in the heteroaryl ring, wherein the heteroatoms are independently chosen from the group consisting of N, O and S; 8, 9 or 10 membered bicyclic heteroaryl containing 1, 2, 3 or 4 heteroatoms, wherein the heteroatoms are independently chosen from the group consisting of N, O and S; heteroaryl-$C_1$-$C_3$ alkyl, wherein the heteroaryl is monocyclic or bicyclic as previously defined;

its stereoisomers, its cosmetically acceptable salts, or mixtures thereof.

18. The composition according to claim 17, wherein the total amount of compounds of formulas (I), (II) and (III) represents from 0.0001% to 5% by weight with respect to the total weight of the composition, and the compounds of formulas (I), (II) and (III) are incorporated into a cosmetically acceptable vehicle or sustained release system chosen from the group consisting of liposomes, millicapsules, microcapsules, nanocapsules, sponges, vesicles, micelles, millispheres, microspheres, nanospheres, microemulsions, nanoemulsions, milliparticles, microparticles, nanoparticles, and solid lipid nanoparticles, are incorporated into hydrolyzed vegetal, animal or synthetic proteins, or are adsorbed onto a cosmetically acceptable solid support chosen from the group consisting of talc, bentonite, silica, starch and maltodextrin, dextran and dextran derivatives.

* * * * *

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Arg Gly Asp Gly Ala Asn Pro Asn Ala Ala Gly
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Arg Gly Asp Gly Pro Gln Gly Pro Gln
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Trp Arg Phe Gln Trp Gln Phe Glu Gln
1               5
```